United States Patent
Tian

(10) Patent No.: US 11,401,509 B2
(45) Date of Patent: Aug. 2, 2022

(54) METHODS OF MINIMIZING GLYCOPROTEIN AGREGATION IN CHO CELL PRODUCTION

(71) Applicant: BRISTOL-MYERS SQUIBB COMPANY, Princeton, NJ (US)

(72) Inventor: Jun Tian, Westford, MA (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 1074 days.

(21) Appl. No.: 15/774,138

(22) PCT Filed: Nov. 7, 2016

(86) PCT No.: PCT/US2016/060782
§ 371 (c)(1),
(2) Date: May 7, 2018

(87) PCT Pub. No.: WO2017/083224
PCT Pub. Date: May 18, 2017

(65) Prior Publication Data
US 2018/0312811 A1    Nov. 1, 2018

Related U.S. Application Data

(60) Provisional application No. 62/252,849, filed on Nov. 9, 2015.

(51) Int. Cl.
*C12N 5/071*    (2010.01)
*C12P 21/00*    (2006.01)
*C12N 5/00*    (2006.01)

(52) U.S. Cl.
CPC ......... *C12N 5/0682* (2013.01); *C12N 5/0031* (2013.01); *C12P 21/005* (2013.01); *C12N 2500/22* (2013.01); *C12N 2500/24* (2013.01); *C12N 2500/32* (2013.01); *C12N 2510/02* (2013.01)

(58) Field of Classification Search
None
See application file for complete search history.

(56) References Cited

U.S. PATENT DOCUMENTS

| 2008/0070280 A1 | 3/2008 | Schilling et al. |
| 2012/0276631 A1 | 11/2012 | Bengea et al. |
| 2014/0273092 A1* | 9/2014 | Flikweert ............... C07K 16/00 435/69.6 |

FOREIGN PATENT DOCUMENTS

| WO | WO 1999061650 | 12/1999 |
| WO | WO 2007050498 | 5/2007 |
| WO | WO 2009126564 | 10/2009 |
| WO | WO 2011134921 | 11/2011 |
| WO | WO 2014062535 | 4/2014 |

OTHER PUBLICATIONS

Bruhlmann D. et al. "Tailoring recombinant protein quality by rational media design", vol. 31, No. 3, Apr. 29, 2015 (Apr. 29, 2015), pp. 615-629.
Gramer M.J. et al.: "Modulation of antibody galactosylation through feeding of uridine, manganese chloride, and galactose", vol. 108, No. 7, Jul. 2011 (Jul. 2011), pp. 1591-1602.
Hossler P. et al.: "Targeted shifting of protein glycosylation profiles in mammalian cell culture through media supplementation of colbalt", J. Glycobiol., vol. 3, No. 1, 108, Sep. 17, 2014 (Sep. 17, 2014), pp. 1-9.

* cited by examiner

*Primary Examiner* — Christian L Fronda
(74) *Attorney, Agent, or Firm* — Brian J. Walsh

(57) ABSTRACT

In accordance with the present invention, CHO cells expressing a recombinant polypeptide of interest are grown in media where the amino acids, vitamins, phosphate, lipids and/or antioxidant optimization is utilized to manipulate and/or control the protein quality attributes of the polypeptides. Polypeptides expressed in accordance with the present invention may be advantageously used in the preparation of pharmaceutical compositions.

7 Claims, 37 Drawing Sheets

US 11,401,509 B2

METHODS OF MINIMIZING GLYCOPROTEIN AGREGATION IN CHO CELL PRODUCTION

This application is the National Stage filed under 35 U.S.C. § 371 of PCT Application No. PCT/US2016/060782, filed Nov. 7, 2016, which claims the benefit of U.S. Patent Application Ser. No. 62/252,849, filed on Nov. 9, 2015, which are herein incorporated by reference in their entirety.

FIELD OF THE INVENTION

The present invention relates to Chinese Hamster Ovary (CHO) cells expressing a recombinant polypeptide of interest grown in media where the amino acids, vitamins, phosphate, lipids and/or antioxidant optimization is utilized to manipulate and/or control the protein quality attributes of the polypeptides. Polypeptides expressed in accordance with the present invention may be advantageously used in the preparation of pharmaceutical compositions.

BACKGROUND OF THE INVENTION

Current ongoing efforts to maximize bioreactor productivity in both time and volume directly affect the scale and capital investment required for a bioreactor suite. As cells reach higher concentrations more quickly, yield is increased; therefore, the number and scale of bioreactors can be reduced. To that end, not only cell engineering, but also culture media and related chemical and physical environments are used to assist cells in reaching peak performance quickly, maintaining a high level as long as possible while producing high quality protein.

Recombinantly produced protein products are increasingly becoming medically and clinically important for use as therapeutics, treatments and prophylactics. Therefore, the development of reliable cell culture processes that economically and efficiently achieve the desired polypeptide attributes is a desired and needed goal in the art.

SUMMARY OF THE INVENTION

The method of the invention is related to the optimization of cell culture media to control and/or mediated protein quality attributes of recombinant glycoprotein expressed in Chinese Hamster Ovary (CHO) cells by changing the level of one or more cell culture media components including but not limit to: growth factors, phosphate, Zn, Fe, amino acids (Asp, Asn, Cys, Ser), lipids, vitamins (B1, B2, B3, B9, B12, Bx), antioxidants (ascorbic acid, glutathione, reduced a-lipoic acid, vitamin E), and combinations thereof.

One embodiment of the invention is controlling protein quality attributes of a recombinant glycoprotein expressed in CHO cells comprising modulating the amount of one or more cell culture media components, such as asparagine, aspartic acid, zinc and iron, wherein glycoprotein aggregation is decreased.

Another embodiment of the invention is controlling protein quality attributes of a recombinant glycoprotein expressed in CHO cells comprising modulating the amount of one or more cell culture media components, such as aspartic acid, phosphate and zinc wherein the sialic acid content of the glycoprotein is increased.

One embodiment of the invention is controlling protein quality attributes of a recombinant glycoprotein expressed in CHO cells comprising modulating the amount of one or more cell culture media components, such as asparagine, zinc and iron, wherein the galactose content of the glycoprotein is increased.

In one embodiment of the invention, the cell culture media is chemically defined. In another embodiment of the invention the cell culture media being optimized is a basal medium.

In one embodiment of the invention, the cell culture medium does not contain added serum or hydrolysates and/or may be protein-free.

The glycoprotein of the invention are recombinant antibodies, antibody fragments or fusion proteins.

DETAILED DESCRIPTION OF THE INVENTION

Figure 1:
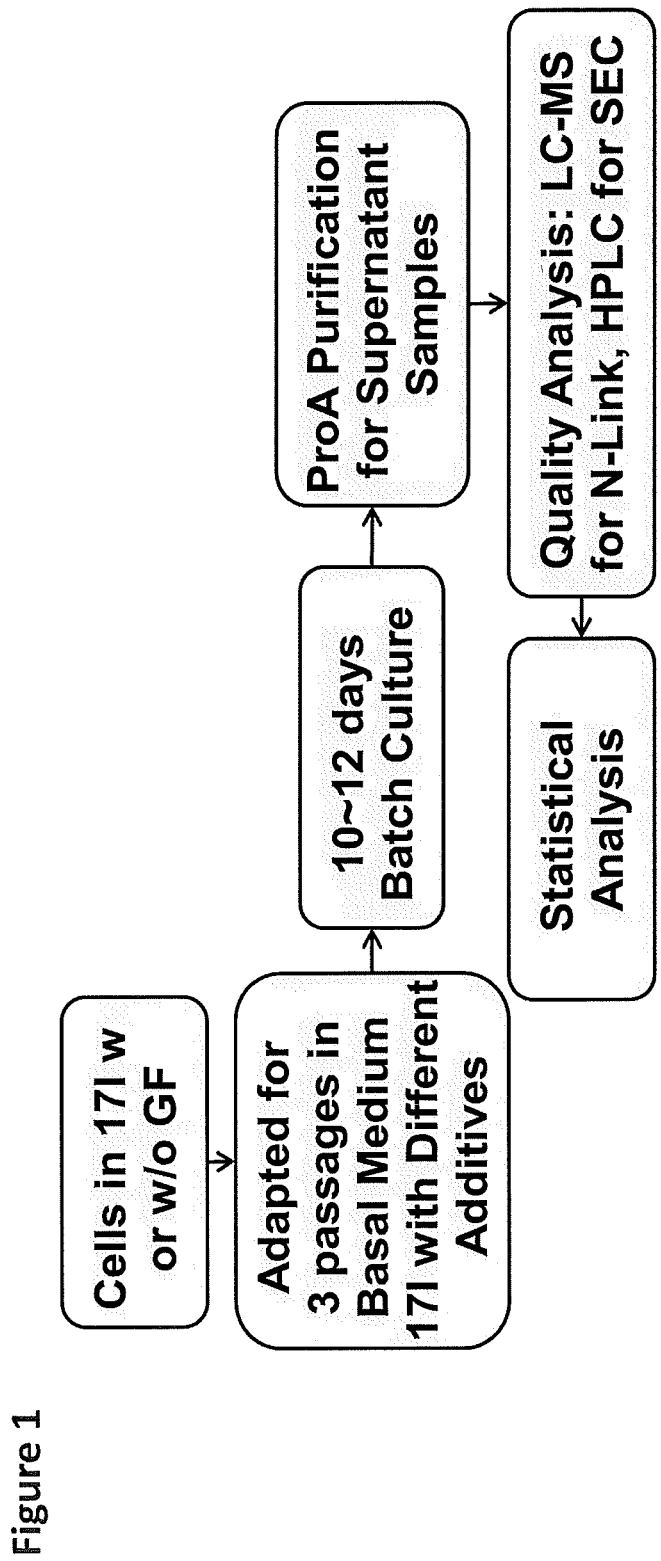
FIG. 1 shows the experimental and analytical flow chart. ProA: protein A
Figure 2:
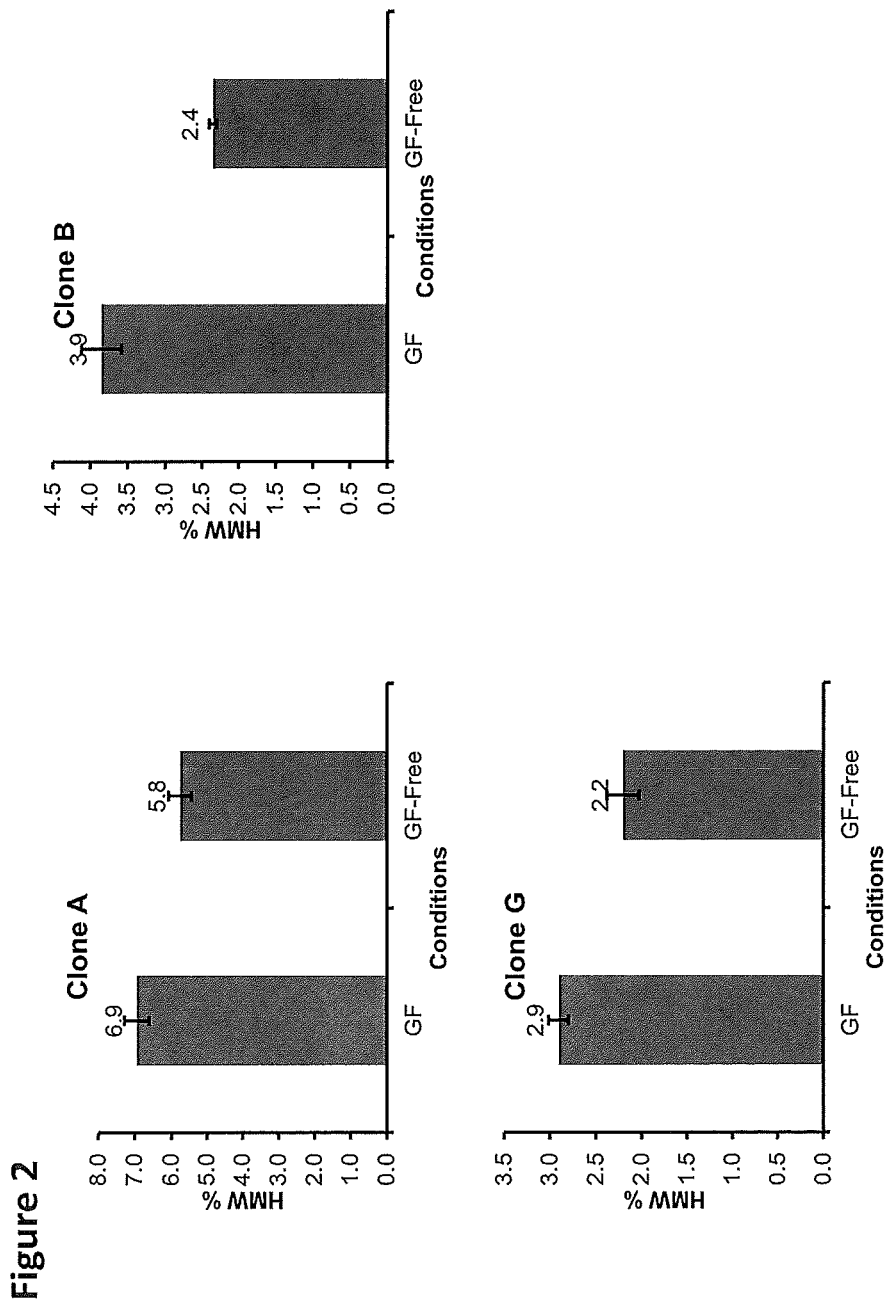
FIG. 2 shows clone A, clone B and clone G cells cultured in the presence of growth factor (1 mg/L insulin) resulted in higher HMW % compared to the cultures without. GF: growth factor; GF-Free: growth factor free FIG. 3A
Figure 3:
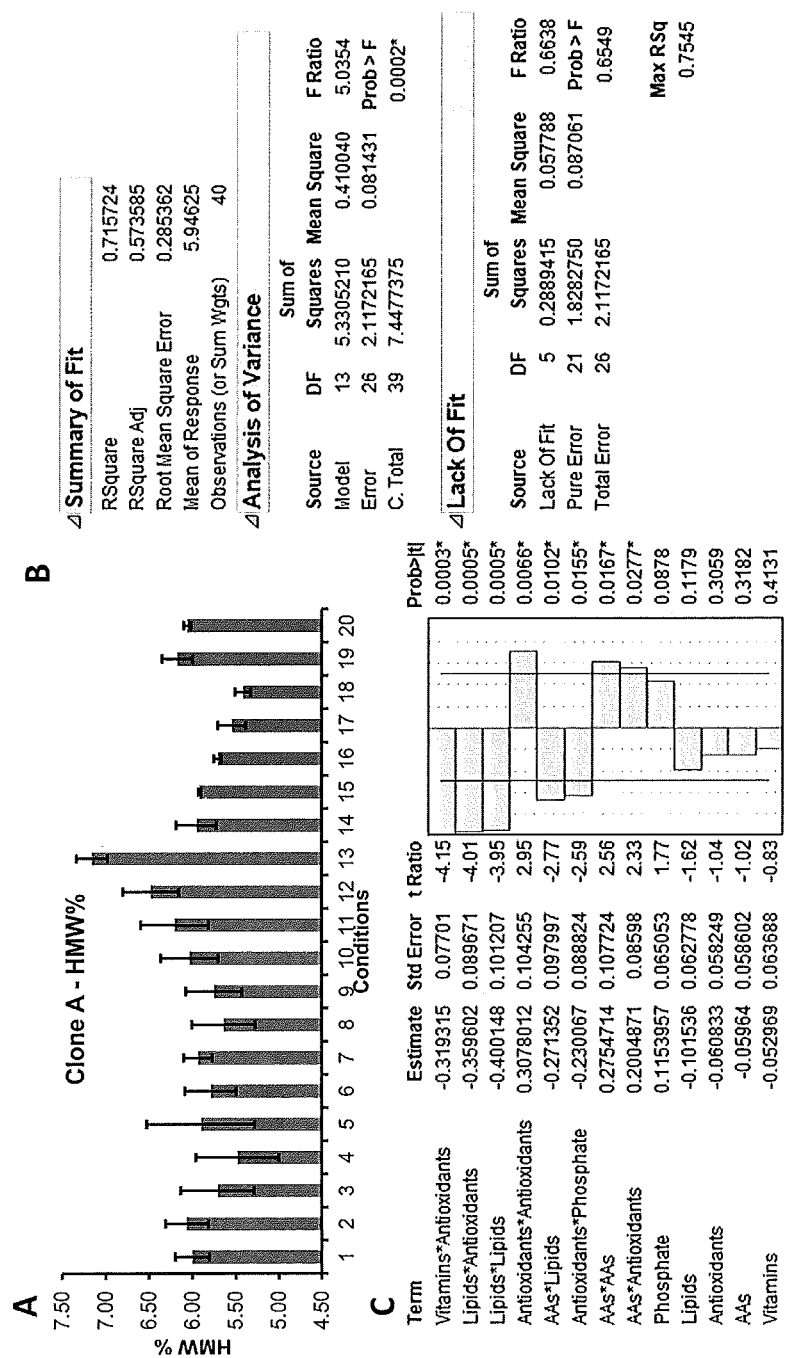
-FIG. 3D shows the statistical analysis of HMW % for cone A. 3A: the levels of HMW % for proteins produced from cells cultured in the prototype media. 3B: statistical summary for the mathematical model generated to fit the data shown in 3A. 3C: List of the major effects of the factors on HMW % and the terms incorporated into the mathematical model. 3D: predicted maximum or minimum HMW % levels using the model generated FIG. 4A
Figure 3:
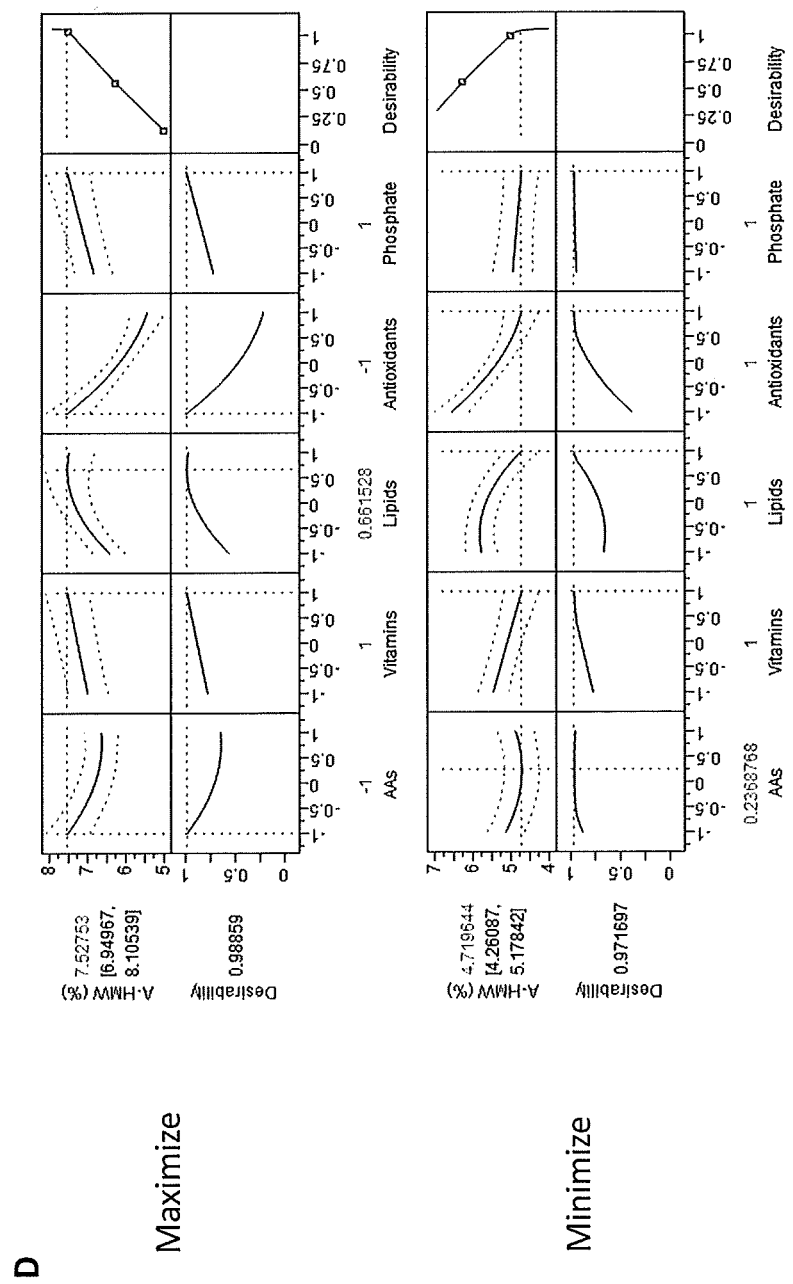
Figure 4:
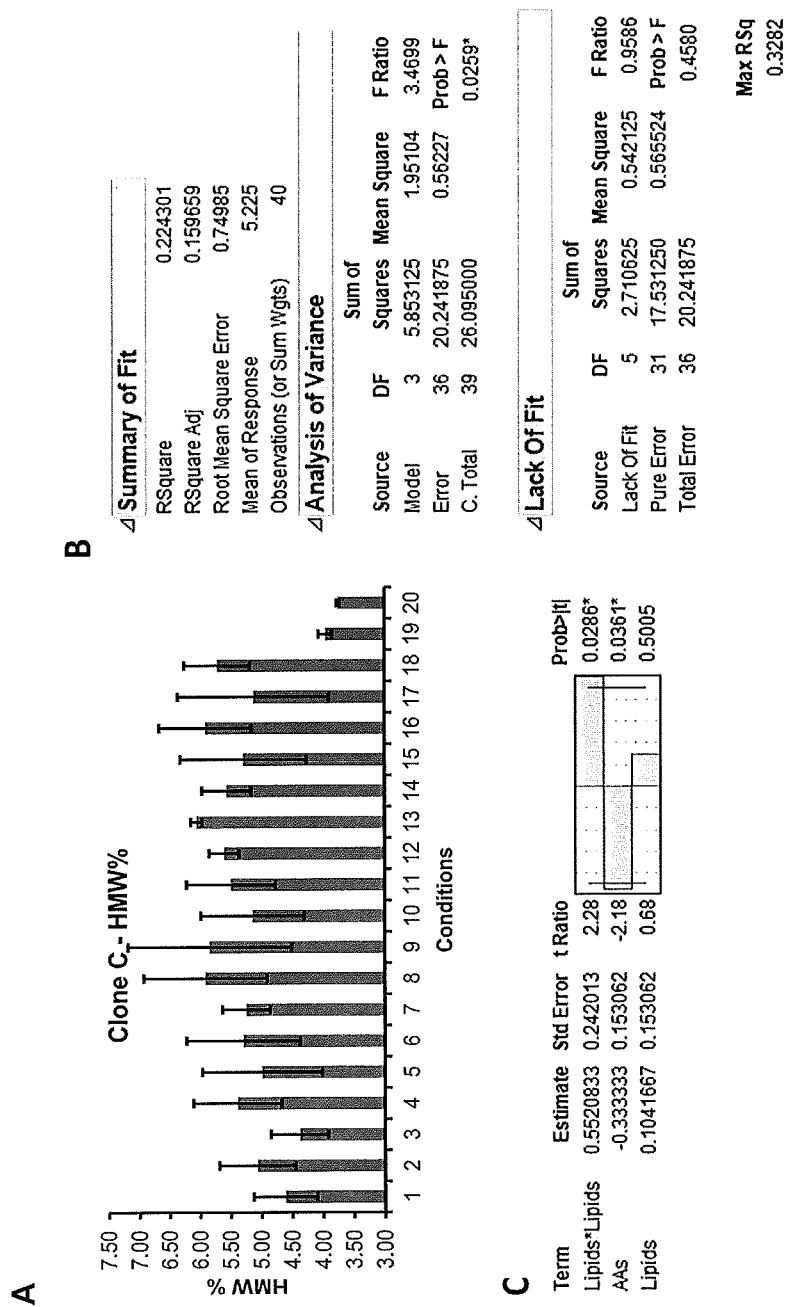
-FIG. 4D shows the statistical analysis of HMW % for clone C. 4A: the levels of HMW % for proteins produced from cells cultured in the prototype media. 4B: statistical summary for the mathematical model generated to fit the data shown in 4A. 4C: List of the major effects of the factors on HMW % and the terms incorporated into the mathematical model. 4D: predicted maximum or minimum HMW % levels using the model generated
Figure 4:
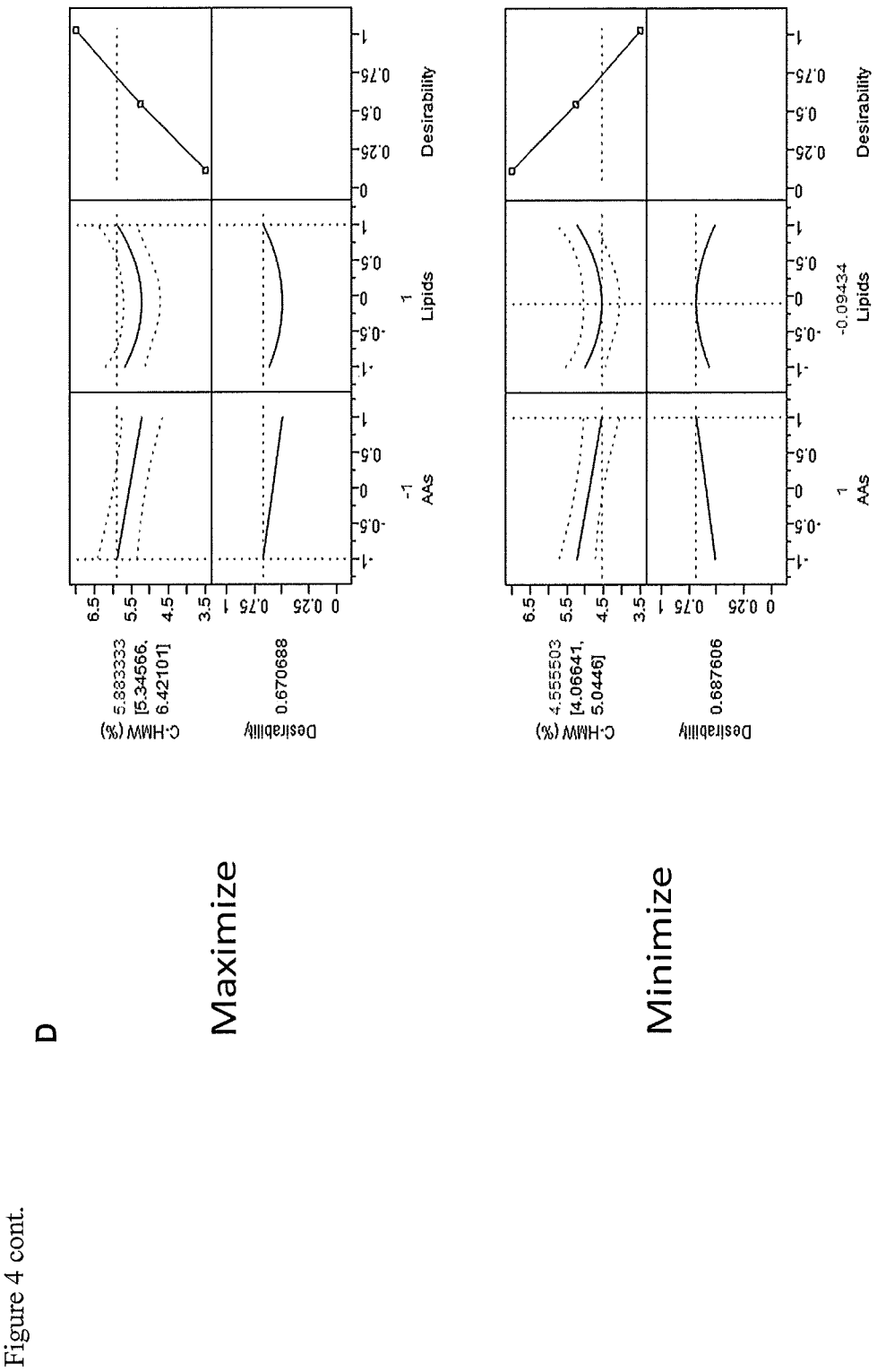
Figure 5:
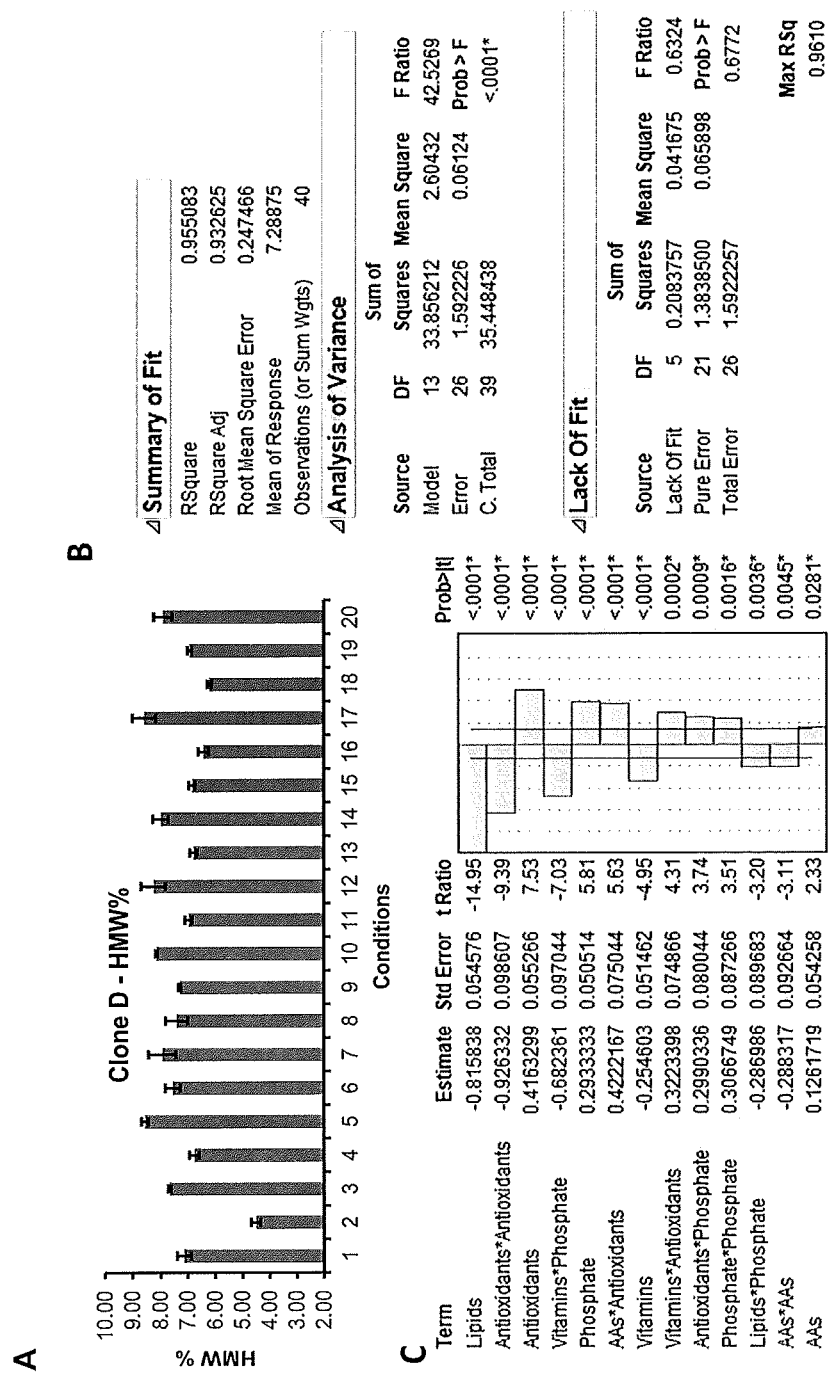
FIG. 5A-FIG. 5D show the statistical analysis of HMW % for clone D. 5A: the levels of HMW % for proteins produced from cells cultured in the prototype media. 5B: statistical summary for the mathematical model generated to fit the data shown in 5A. 5C: List of the major effects of the factors on HMW % and the terms incorporated into the mathematical model. 5D: predicted maximum or minimum HMW % levels using the model generated
Figure 5:
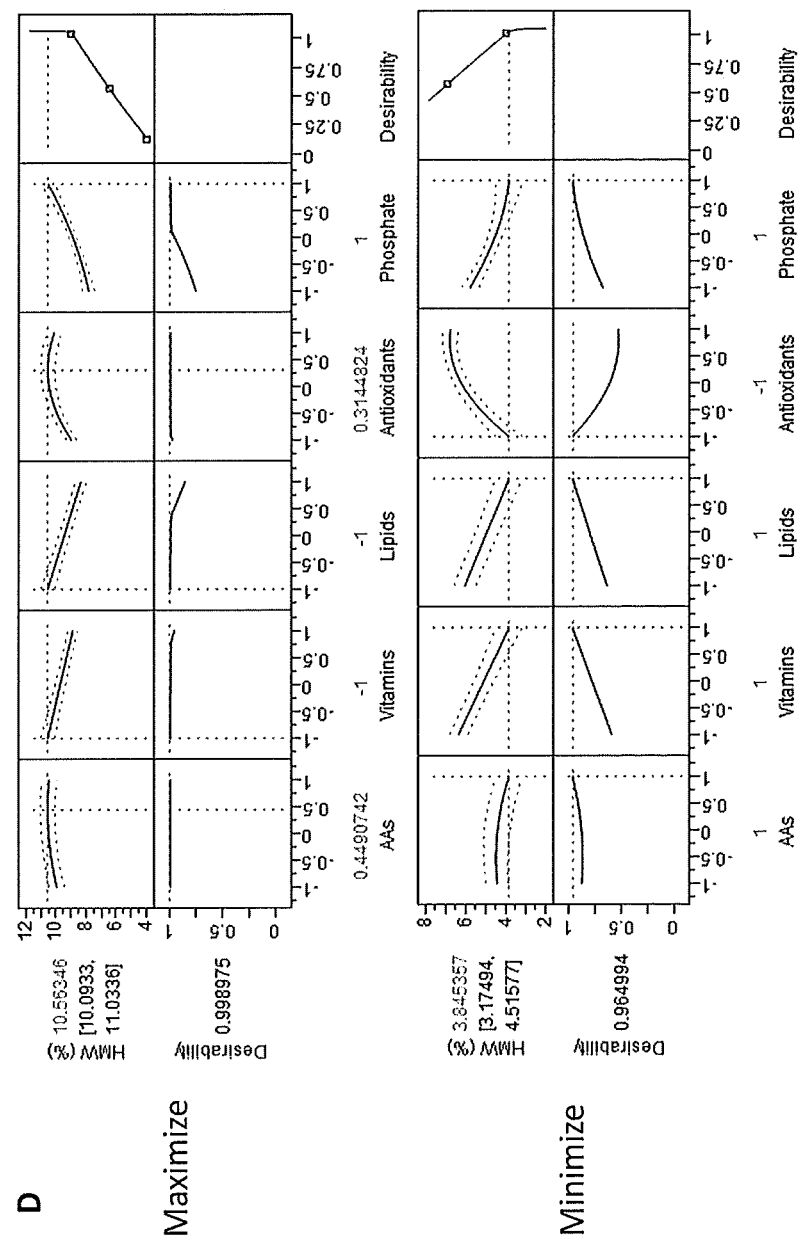
Figure 6:
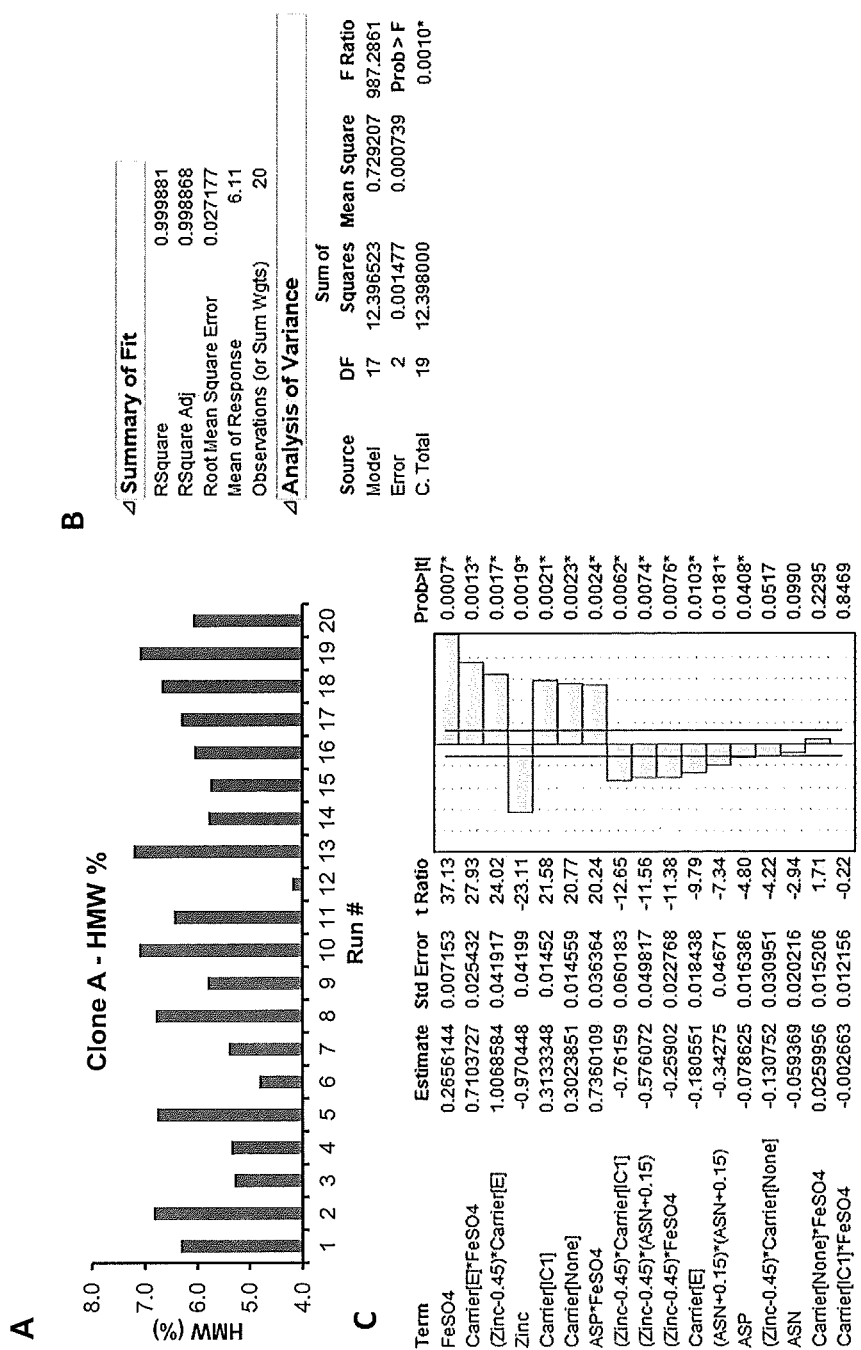
FIG. 6A-FIG. 6D show the statistical analysis of HMW % for clone A. 6A: the levels of HMW % for proteins produced from cells cultured in the prototype media. 6B: statistical summary for the mathematical model generated to fit the data shown in 6A. 6C: List of the major effects of the factors on HMW % and the terms incorporated into the mathematical model. 6D: predicted maximum or minimum HMW % levels using the model generated
Figure 6:
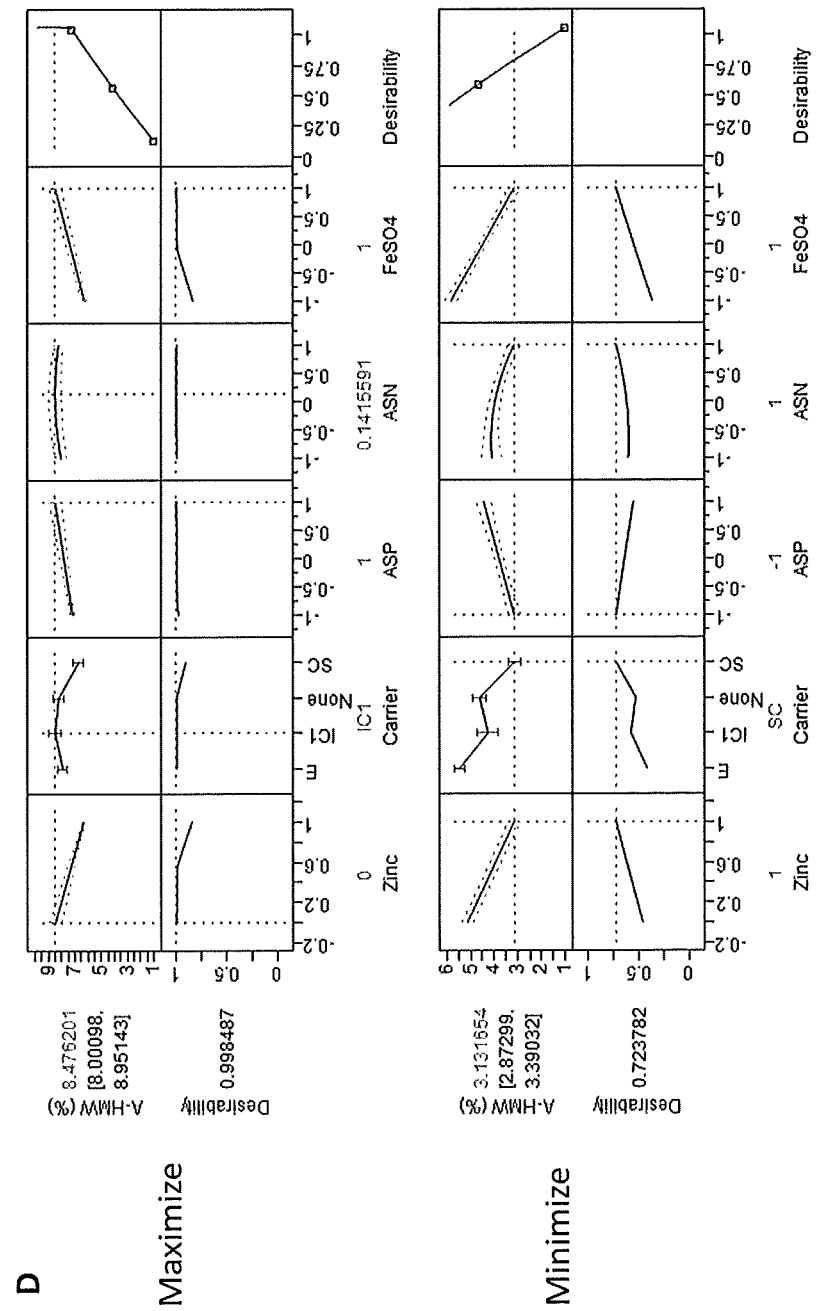

The present invention relates to new methods to manipulate and/or control the protein quality attributes of polypeptides produced in Chinese Hamster Ovary (CHO) cell cultures by changing the level of specific medium components including but not limit to: growth factors, phosphate, Zn, Fe, amino acids (Asp, Asn, Cys, Ser), lipids, vitamins (B1, B2, B3, B9, B12, Bx), and combinations thereof. As described herein, a variety of media are encompassed by the present invention.

As used herein, the term "basal medium" and "basal media" refers to starting medium to which cells are added to begin the culture. Basal media is a solution containing nutrients that nourish growing cells. Typically, a basal medium provides essential and non-essential amino acids, vitamins, energy sources, lipids, and trace elements required by the cell for minimal growth and/or survival. A basal medium may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In certain embodiments, a basal medium is advantageously formulated to manipulate and/or maintain recombinant polypeptide quality attributes, such as percent high molecular weight (HMW %), percent galactose (Gal %), percent sialic acid (SA %), and percent mannose (Man %) Exemplary basal media components are shown in Table 1.

As used herein, the term "amino acid" refers to any of the twenty naturally occurring amino acids that are normally used in the formation of polypeptides, analogs or derivatives of those amino acids or any non-naturally occurring amino acid. In certain embodiments, amino acids of the present invention are provided in medium to cell cultures. The amino acids provided in the medium may be provided as salts or in hydrate form.

As used herein the term "defined medium" refers to a medium in which the composition of the medium is both known and controlled. In certain embodiments, basal media is a defined medium.

As used herein the term "glycoprotein" refers to a protein or polypeptide that contains one or more covalently linked oligosaccharide chains. The oligosaccharide chains may be composed of a single sugar residue, a single unbranched chain of sugar residues or a chain of sugar residues that branches one or more times. The oligosaccharide chains may be either N-linked or O-linked.

As used herein the term "glycosylation pattern" refers to the observed glycosylation of a given glycoprotein or glycoproteins. A glycoprotein with a greater number of covalently linked sugar residues in its oligosaccharide chain(s) is said to have an increased or more extensive glycosylation pattern. Conversely, a glycoprotein with fewer covalently linked sugar residues in its oligosaccharide chain(s) is said to have a decreased or less extensive glycosylation pattern. The term "glycosylation pattern" as used herein also refers to a characteristic distribution of several different glycosylation patterns on individual glycoproteins expressed according to the teachings of the present invention. In this sense, an increased glycosylation pattern refers to an increase in the characteristic distribution of glycosylation patterns of the expressed glycoproteins.

As used herein "recombinantly expressed polypeptide" and recombinant polypeptide" refer to a polypeptide expressed from a host cell that has been manipulated by the hand of man to express that polypeptide. In certain embodiments, the host cell is Chinese Hamster Ovary cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g. heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes. In certain embodiments, the recombinantly expressed polypeptide is an antibody. In certain embodiments, the recombinantly expressed polypeptide is an antibody fragment (dAb).

Screening of Media Components

The media components were grouped into amino acids, vitamins, lipids, antioxidants, and phosphate based on the functions or properties for the chemical compounds. The groups were then the study factors used to generate prototype media conditions shown in Example 2 using a response surface statistical design approach. Cells were cultured in the prototype media without any growth factors following the protocol described in Example 1.

TABLE 1

| Grouped components, levels and concentration range thereof (Example 2) | | | | | |
|---|---|---|---|---|---|
| Group | Components | Level 1 (Coded) | Level 2 (Coded) | Level 3 (Coded) | Concentration Range |
| Amino Acids | L-Aspartic Acid | 0 (−1) | +250% (0) | +500% (+1) | 0.1-2 g/L |
| | L-Cysteine | 0 (−1) | +50% (0) | +100% (+1) | 0.1-2 g/L |
| | L-Serine | 0 (−1) | +25% (0) | +50% (+1) | 0.1-2 g/L |
| Vitamins | Niacinamide (B3) | 0 (−1) | +25% (0) | +50% (+1) | 0.01-100 mg/L |
| | p-Aminobenzoic Acid (Bx, PABA) | 0 (−1) | +25% (0) | +50% (+1) | 0.01-100 mg/L |
| | Riboflavin (B2) | 0 (−1) | +25% (0) | +50% (+1) | 0.01-100 mg/L |
| | Thiamine (B1) | 0 (−1) | +50% (0) | +100% (+1) | 0.01-100 mg/L |
| Phosphate | Sodium Phosphate | 0 (−1) | +50% (0) | +100% (+1) | 0.1-2 g/L |
| Lipids | Phosphotydylcholine | | Proprietary | | |
| | Proprietary | | Proprietary | | |
| Antioxidants | Ascorbic Acid | 0 (−1) | +75% (0) | +150% (+1) | 0.01-100 mg/L |
| | Glutathione, reduced | 0 (−1) | +200% (0) | +400% (+1) | 0.01-100 mg/L |
| | a-Lipoic Acid | 0 (−1) | +50% (0) | +100% (+1) | 0.01-100 mg/L |
| | Vitamin E | 0 (−1) | +50% (0) | +100% (+1) | 0.01-100 mg/L |

Factors Impacting HMW %

Aggregation is a concern in biological manufacturing inasmuch as aggregated protein in the final product may affect biological activity and has been linked to the development of adverse immunological responses (Rosenberg A S. Effects of Protein Aggregates: An Immunologic Perspective. AAPS J 2006; 8 (3) E501-7).

Table 2 below summarizes the effects of a single factor on percent high molecular weight (HMW %) across the different clones.

TABLE 2

Effect of Single Factor on HMW %

| Clone | Amino Acids | Phosphate | Lipids | Antioxidants | Vitamins | FeSO4 | Zn | Asn | Asp | Growth Factors |
|---|---|---|---|---|---|---|---|---|---|---|
| A | NE | NE | NE | NE | NE | ↑ | ↓ | NE | ↓ | ↑ |
| B | NM | NM | NM | NM | NM | NE | ↓ | ↑ | NE | ↑ |
| C | ↓ | NE | NE | NE | NE | NM | NM | NM | NM | NM |
| D | ↑ | ↑ | ↓ | ↑ | ↓ | NM | NM | NM | NM | NM |
| G | NM | NM | NM | NM | NM | NM | NM | NM | NM | ↑ |

NE: No Effect
NM: No Measurement

While the addition of growth factors generally increased (↑) the HMW %, the addition of zinc generally decreased (↓) HMW %. In clone D, the addition of amino acids, phosphate or antioxidants increased HMW % and the addition of lipids or vitamins decreased HMW %.

Table 3 below summarizes the combined factors that have an effect on HMW % in three of the studied clones. The predictions are based on relative ranges: −1 is the lower range, 0 is the middle, and +1 is the higher range. All of the ranges are relative to the components in the media formulation.

TABLE 3

Effect of Combined Factors on HMW %

| | | | Concentration Levels | | | | |
|---|---|---|---|---|---|---|---|
| | | Prediction HMW % | Amino | | | | |
| Clone | Target | Level [Range] | Acids | Phosphate | Lipids | Antioxidants | Vitamins |
| A | Max | 7.53 [6.95, 8.11] | −1 | 1 | 0.66 | −1 | 1 |
| | Min | 4.72 [4.26, 5.18] | 0.24 | 1 | 1 | 1 | 1 |
| C | Max | 5.88 [5.34, 6.42] | −1 | 1 | N/A | N/A | N/A |
| | Min | 4.56 [4.07, 5.04] | 1 | −0.1 | N/A | N/A | N/A |
| D | Max | 10.56 [10.10, 11.03] | 0.45 | 1 | −1 | −0.31 | −1 |
| | Min | 3.85 [3.17, 4.52] | 1 | 1 | 1 | −1 | 1 |

In the case of clone A, the HMW % level could be minimized at a mean value of 4.72% with a 95% chance the HMW % will be in the range of 4.26 to 5.18. However, if the levels for amino acids, lipids, or antioxidants are not properly set, the HMW % could increase to as high as 8.11%.

In the case of clone C, the HMW % level could be minimized at a mean value of 4.56% with a 95% chance the HMW % will be in the range of 4.07 to 5.04. However, if the levels for amino acids or phosphate are not properly set, the HMW % could increase to as high as 6.42%.

In the case of clone D, the HMW % level could be minimized at a mean value of 3.85% with a 95% chance the HMW % will be in the range of 3.17 to 4.52. However, if the levels for amino acids lipids, antioxidants or vitamin are not properly set, the HMW % could increase to as high as 11.03%.

Table 4 below summarizes the effects specific ingredients have on HMW % in clone A and B.

TABLE 4

Effect of Combined Factors on HMW %

| | | | Concentration Levels | | | | |
|---|---|---|---|---|---|---|---|
| | | Prediction HMW % | | | | Iron | |
| Clone | Target | Level [Range] | Zn | Asn | FeSO4 | Carrier | Asp |
| A | Max | 8.48 [8.00, 8.95] | 0 | 0.14 | 1 | IC1 | 1 |
| | Min | 3.13 [2.87, 3.39] | 1 | 1 | 1 | SC | −1 |

TABLE 4-continued

Effect of Combined Factors on HMW %

| | | | Concentration Levels | | | | |
|---|---|---|---|---|---|---|---|
| | | Prediction HMW % | | | | Iron | |
| Clone | Target | Level [Range] | Zn | Asn | FeSO4 | Carrier | Asp |
| B | Max | 6.48 [5.40, 7.54] | 0 | 1 | −1 | N/A | 1 |
| | Min | 1.39 [0.00, 2.81] | 1 | 1 | 0.04 | N/A | −1 |

In the case of clone A, the HMW % level could be minimized at a mean value of 3.13% when zinc, Asn and Asp were controlled at 1, 1, −1, respectively, with a 95% chance the HMW % will be in the range of 2.87 to 3.39.

However, if the levels for Asn, Asp or zinc are not properly set, the HMW % could increase to as high as 8.95%.

In the case of clone B, the HMW % level could be minimized at a mean value of 1.39% when zinc, FeSO4 and Asp were controlled at 1, 0.04, −1, respectively, with a 95% chance the HMW % will be in the range of 0 to 2.81. However, if the levels for Asp, zinc or FeSO4 are not properly set, the HMW % could increase to as high as 7.54%.

Glycosylation

Glycosylation is the most common post-translational modification of proteins. It is a complex process involving many functional proteins and resulting in a great diversity of carbohydrate-protein bonds and glycan structures. Glycosylation of some proteins has a great impact on their structures, functions, stability and serum clearance rates, which all impact efficacy.

Structurally, glycoproteins consist of a polypeptide covalently bonded to a carbohydrate moiety. The carbohydrate can make up anywhere from less than one percent to more than 80 percent of the total protein mass. The saccharide chains, referred to as glycans, can be linked to the polypeptide in two major ways. The first class of glycoproteins are the O-linked glycans. These usually contain an N-acetylgalactosamine which is attached through a glycosidic bond to the O-terminus of either threonine or serine. The other class of glycoproteins are the N-linked glycans. These involve a glycosidic bond between N-acetylglucosamine and the N-terminus of an asparagine residue (Schulz, Georg E. And R. H. Schirmer. Principles of Protein Structure. Springer-Verlag: New York, 1979. P. 228-230).

Attached to the N-acetylgalactosamine or N-acetylglucoseamine is one or more mannose, and galactose residues, with a sialic acid residue occupying the terminal positions of the oligosaccharide chains.

Factors Impacting Gal %

Table 5 below summarizes the effects of a single factor on percent galactose (Gal %) across the different clones.

TABLE 5

Effect of Single Factor on Gal %

| Clone | Amino Acids | Phosphate | Lipids | Antioxidants | Vitamins | FeSO4 | Zn | Asn | Growth Factors |
|---|---|---|---|---|---|---|---|---|---|
| A | ↓ | ↑ | NE | NE | NE | ↓ | ↑ | ↓ | ↓ |
| B | ↓ | ↓ | NE | NE | NE | NM | NM | NM | ↓ |
| C | ↓ | NE | NE | NE | NE | NM | NM | NM | NM |
| D | NE | ↑ | ↓ | ↑ | ↑ | NM | NM | NM | ↓ |
| F | NM | NM | NM | NM | NM | ↑ | NE | ↓ | NM |
| G | NM | ↑ | NM | NM | NM | NM | NM | NM | ↓ |

NE: No Effect
NM: no measurement

While the addition of amino acids, specifically Asn or growth factors generally decreased (↓) the Gal %, the addition of zinc, vitamins and antioxidants generally increased (↑) Gal %. In clone D, the addition of phosphate, vitamins or antioxidants increased Gal % and the addition of lipids or growth factors decreased Gal %.

Table 6 below summarizes the combined factors that have an effect on Gal % in clones A-D. The predictions are based on relative ranges: −1 is the lower range, 0 is the middle, and +1 is the higher range. All of the ranges are relative to the components in the media formulation.

TABLE 6

Effect of Combined Factors on Gal %

| | | Prediction Gal % | Concentration Levels | | | | |
|---|---|---|---|---|---|---|---|
| Clone | Target | Level [Range] | Amino Acids | Phosphate | Lipids | Antioxidants | Vitamins |
| A | Max | 34.15 [31.34, 36.96] | −1 | 1 | 1 | 1 | 1 |
|  | Min | 9.27 [6.26, 12.28] | 1 | −1 | −1 | 1 | 1 |
| B | Max | 116.77 [113.22, 120.33] | −1 | −1 | | | |
|  | Min | 106.75 [103.26, 110.24] | 1 | 1 | | | |
| C | Max | 17.74 [16.19, 19.29] | −1 | | −1 | 1 | −1 |
|  | Min | 9.94 [8.50, 11.37] | 1 | | 1 | 1 | −1 |
| D | Max | 38.56 [36.75, 40.37] | −1 | 1 | −1 | 1 | 1 |
|  | Min | 13.80 [12.63, 14.97] | −1 | 1 | 1 | −1 | −1 |

In the case of clone A, the Gal % level could be maximized at a mean value of 34.14% with a 95% chance the Gal % will be in the range of 31.34 to 36.96%. However, if the levels for amino acids, phosphate or lipids are not properly set, the Gal % could decrease to as low as 6.26%.

In the case of clone B, the Gal % level could be maximized at a mean value of 116.77% with a 95% chance the Gal % will be in the range of 113.22 to 120.33%. However, if the levels for amino acids or phosphate are not properly set, the Gal % could decrease to as low as 103.26%.

In the case of clone C, the Gal % level could be maximized at a mean value of 17.74% with a 95% chance the Gal % will be in the range of 16.19 to 1929%. However, if the levels for amino acids or lipids are not properly set, the Gal % could decrease to as low as 8.50%.

In the case of clone D, the Gal % level could be maximized at a mean value of 38.56% with a 95% chance the Gal % will be in the range of 36.75 to 40.37%. However, if the levels for lipids, antioxidants or vitamins are not properly set, the Gal % could decrease to as low as 12.63%.

Table 7 below summarizes the effects specific ingredients have on Gal % in clone A, B and F.

Figure 7:
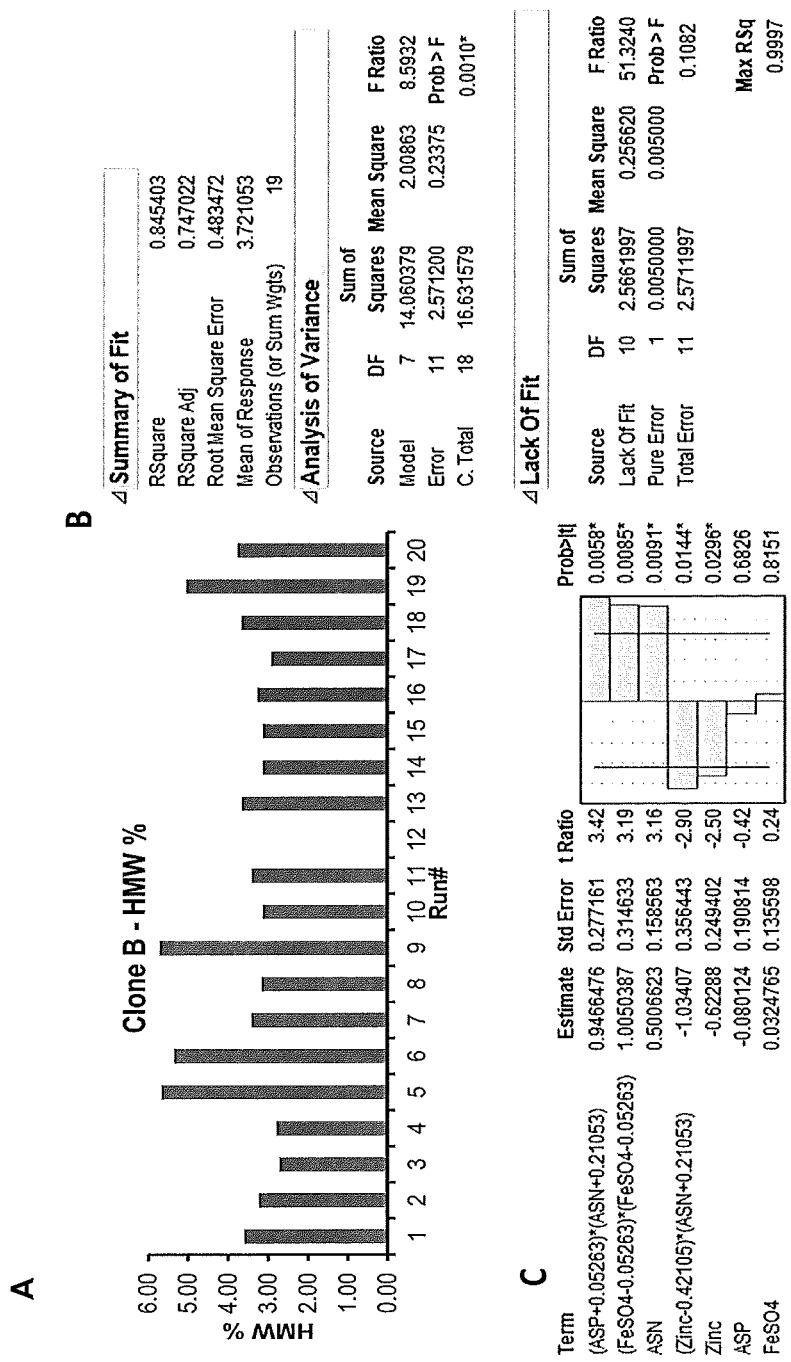
FIG. 7A-FIG. 7D show the statistical analysis of HMW % for clone B. 7A: the levels of HMW % for proteins produced from cells cultured in the prototype media. 7B: statistical summary for the mathematical model generated to fit the data shown in 7A. 7C: List of the major effects of the factors on HMW % and the terms incorporated into the mathematical model. 7D: predicted maximum or minimum HMW % levels using the model generated
Figure 7:
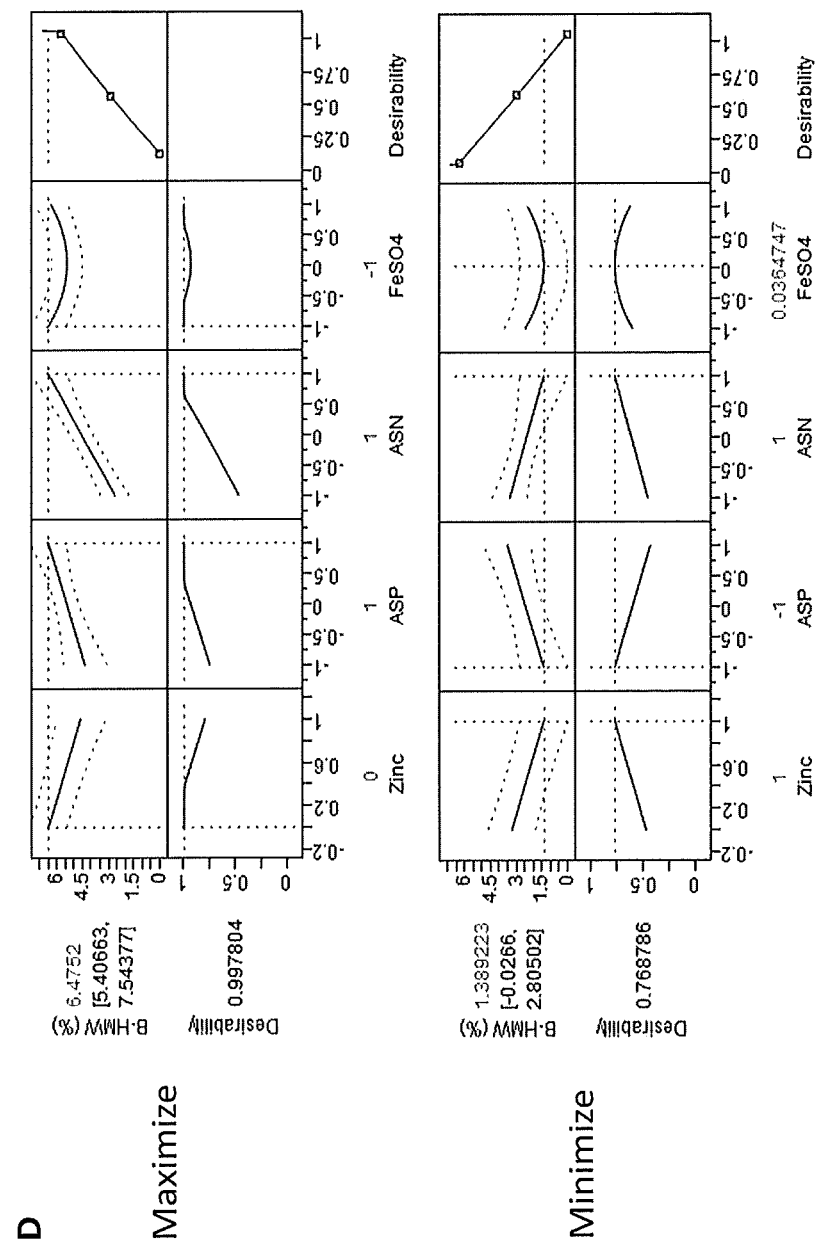
Figure 8:
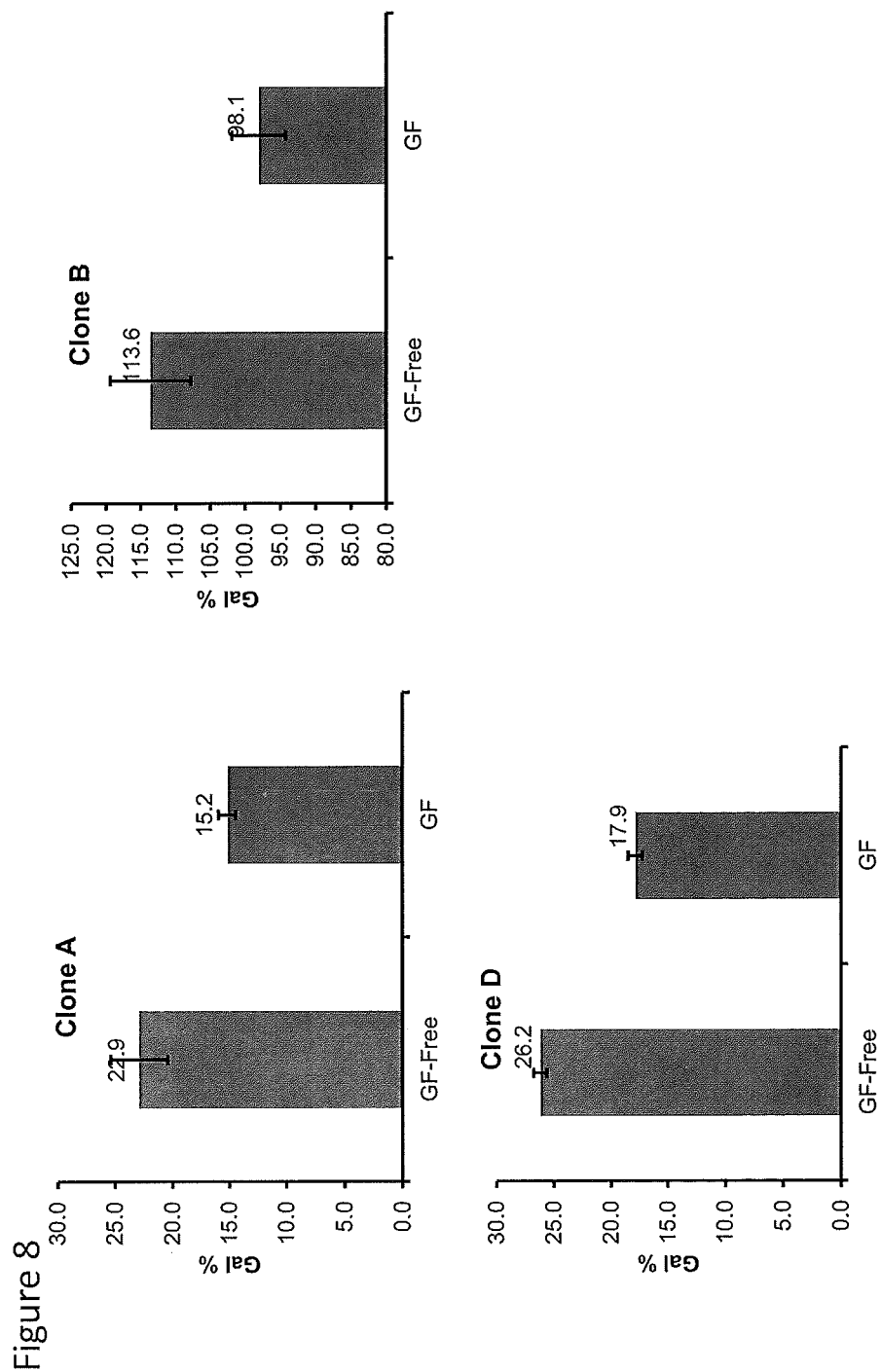
FIG. 8 shows clone A, clone B and clone D cells cultured in the presence of growth factor (1 mg/L insulin) resulted in lower gal % compared to the cultures without. GF: growth factor; GF-Free: growth factor free.
Figure 9:
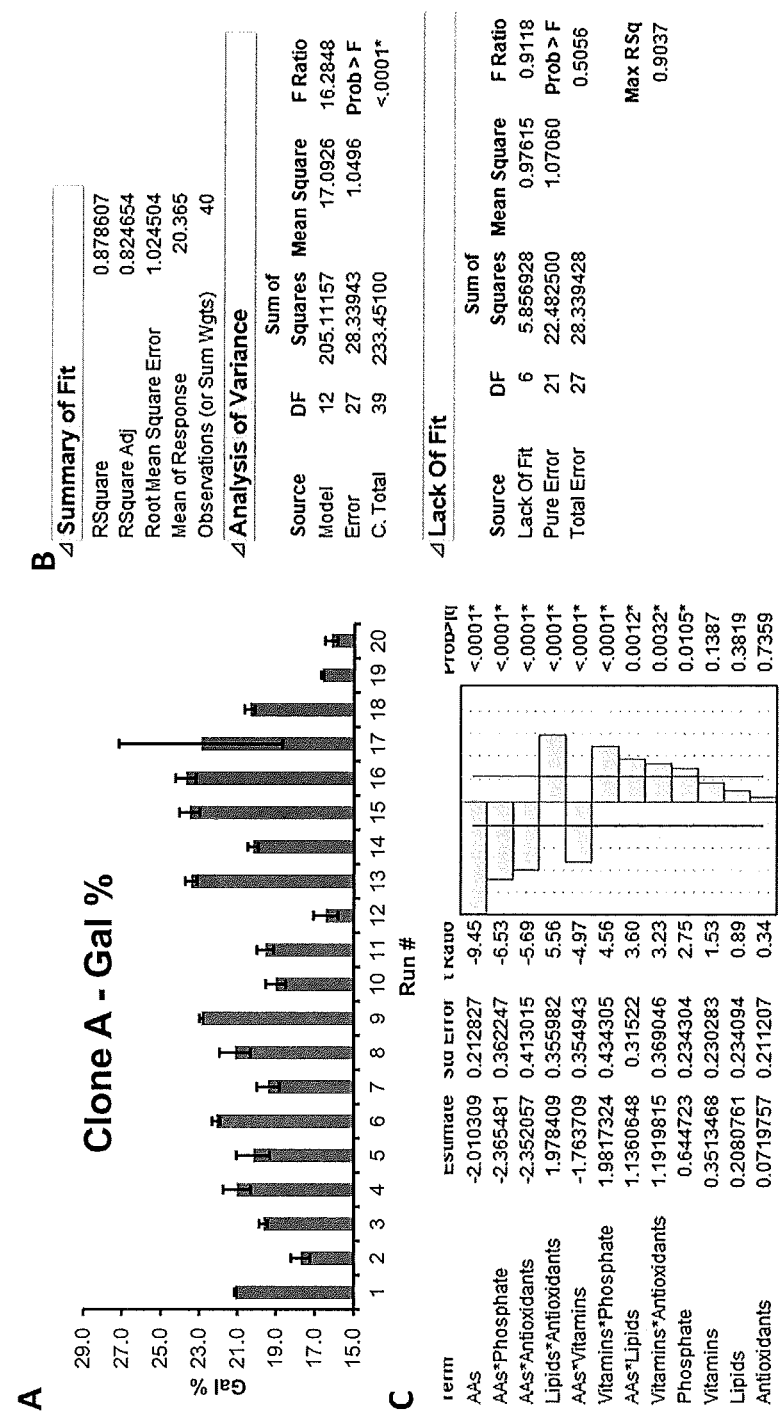
FIG. 9A-FIG. 9D show the statistical analysis of gal % for clone A. 9A: the levels of gal % for proteins produced from cells cultured in the prototype. 9B: statistical summary for the mathematical model generated to fit the data shown in 9A. 9C: List of the major effects of the factors on gal % and the terms incorporated into the mathematical model. 9D: predicted maximum or minimum gal % levels using the model generated
Figure 9:
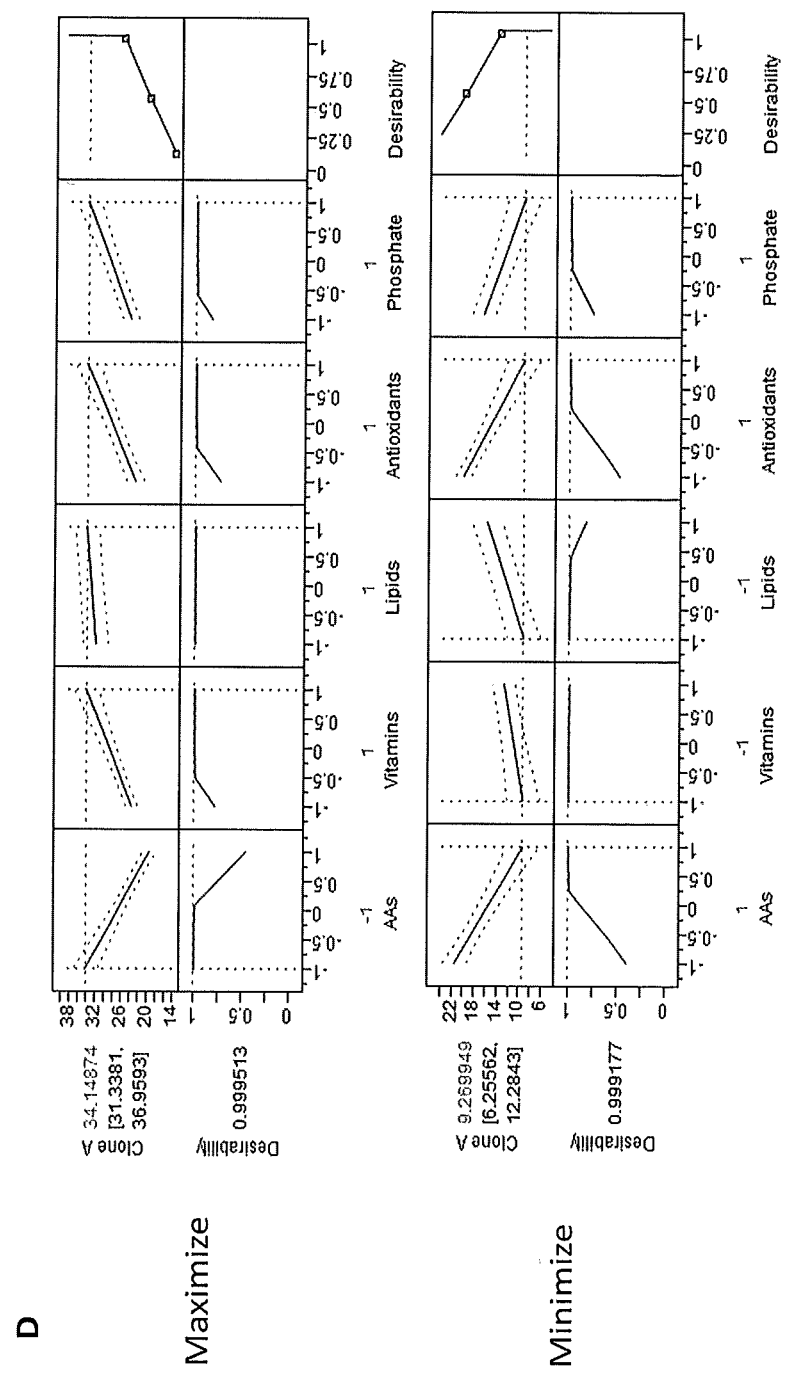
Figure 10:
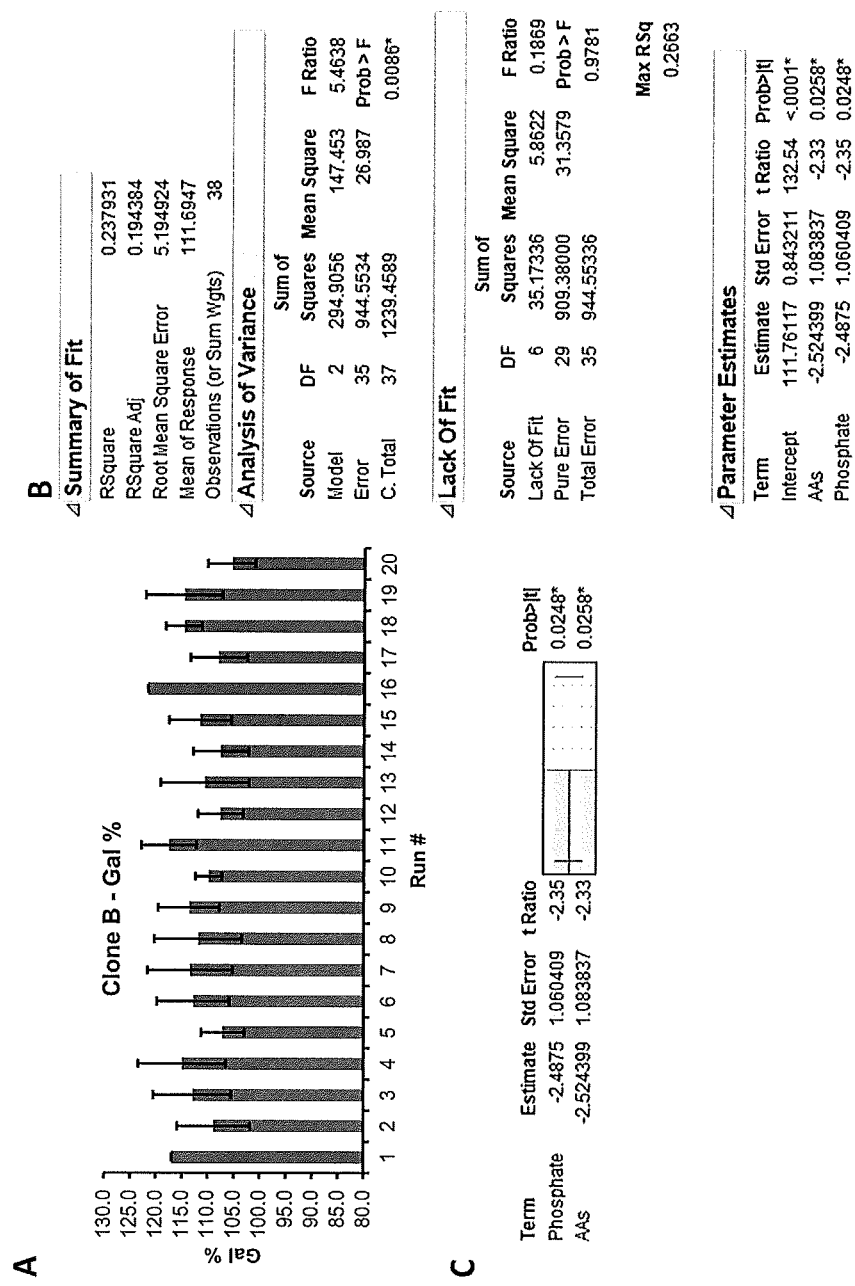
FIG. 10A-FIG. 10D show the statistical analysis of gal % for clone B. 10A: the levels of gal % for proteins produced from cells cultured in the prototype media. 10B: statistical summary for the mathematical model generated to fit the data shown in 10A. 10C: List of the major effects of the factors on gal % and the terms incorporated into the mathematical model. 10D: predicted maximum or minimum gal % levels using the model generated
Figure 10:
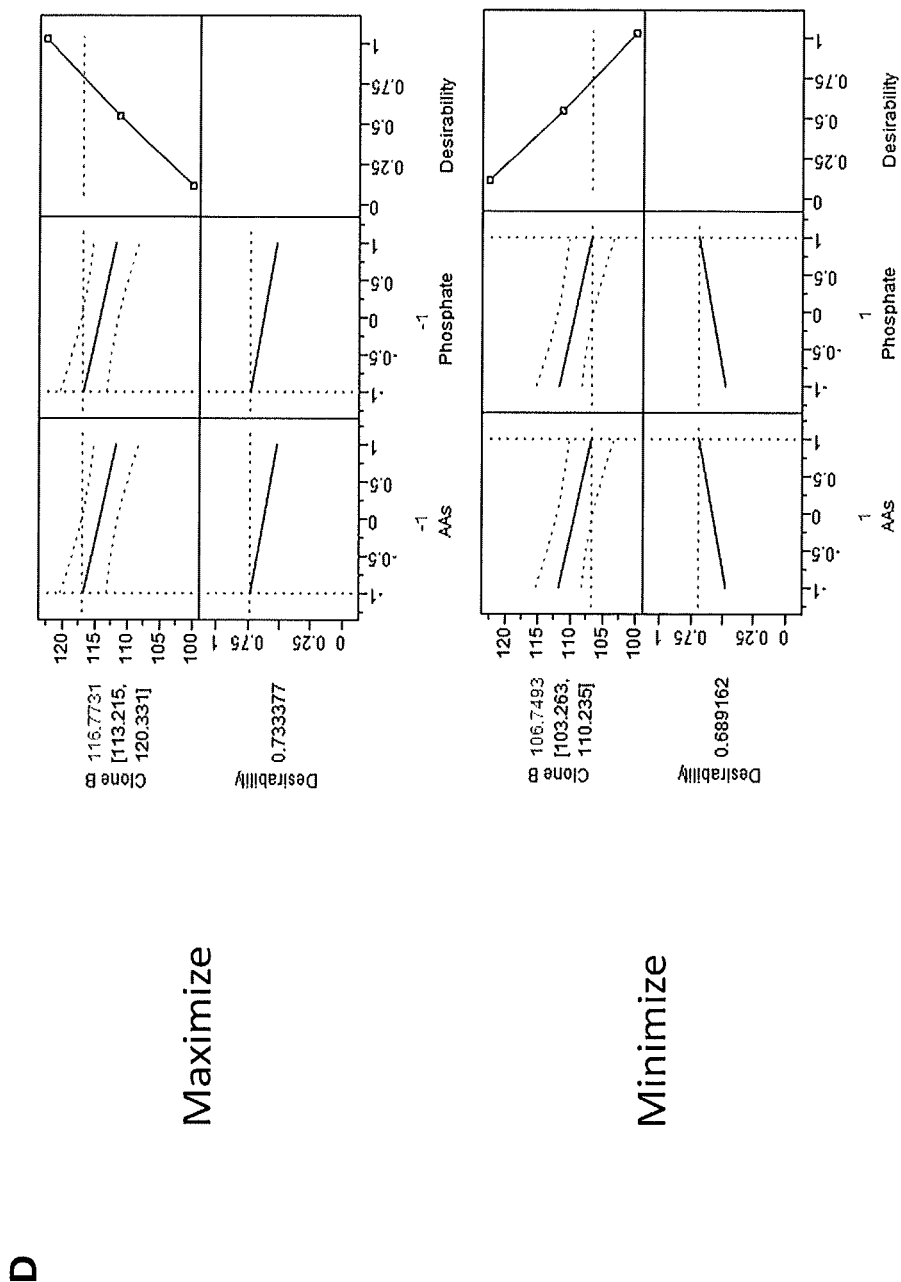
Figure 11:
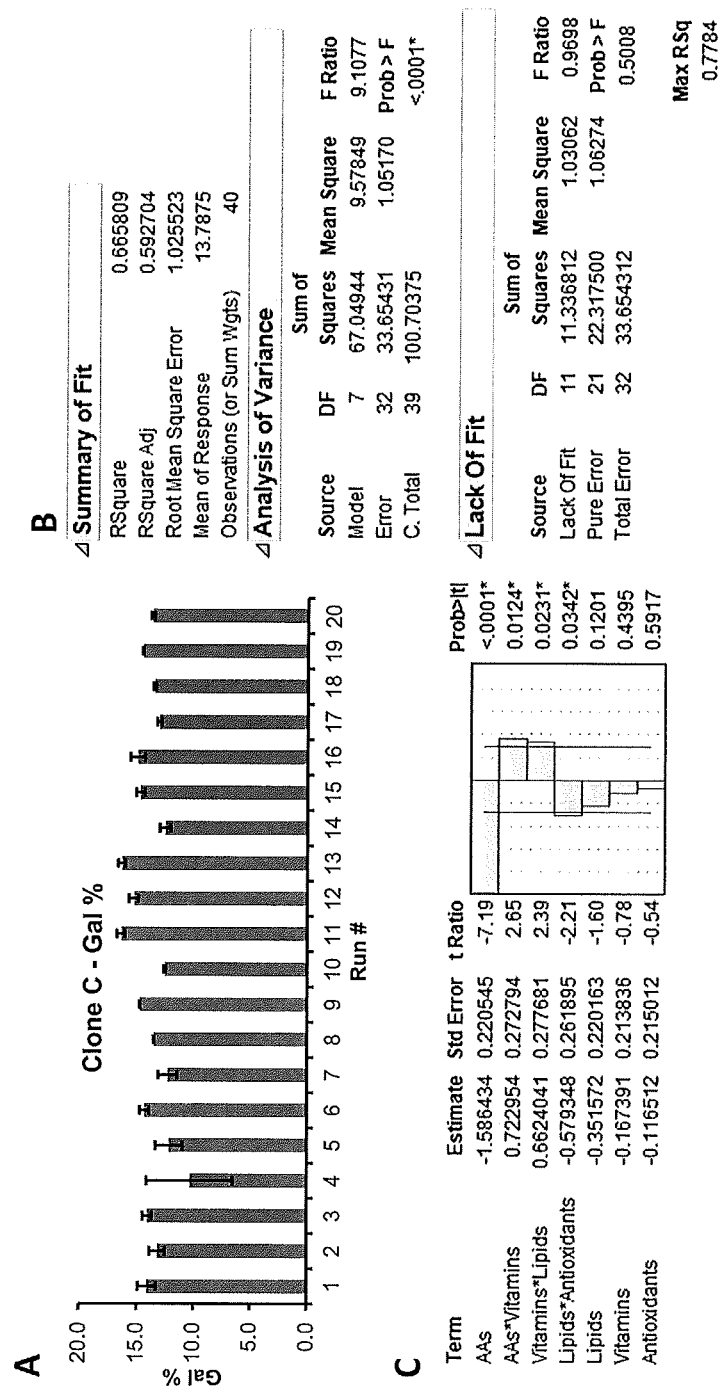
FIG. 11A-FIG. 11D: Statistical Analysis of gal % for clone C. 11A: the levels of gal % for proteins produced from cells cultured in the prototype media. 11B: statistical summary for the mathematical model generated to fit the data shown in 11A. 11C: List of the major effects of the factors on gal % and the terms incorporated into the mathematical model. 11D: predicted maximum or minimum gal % levels using the model generated
Figure 11:
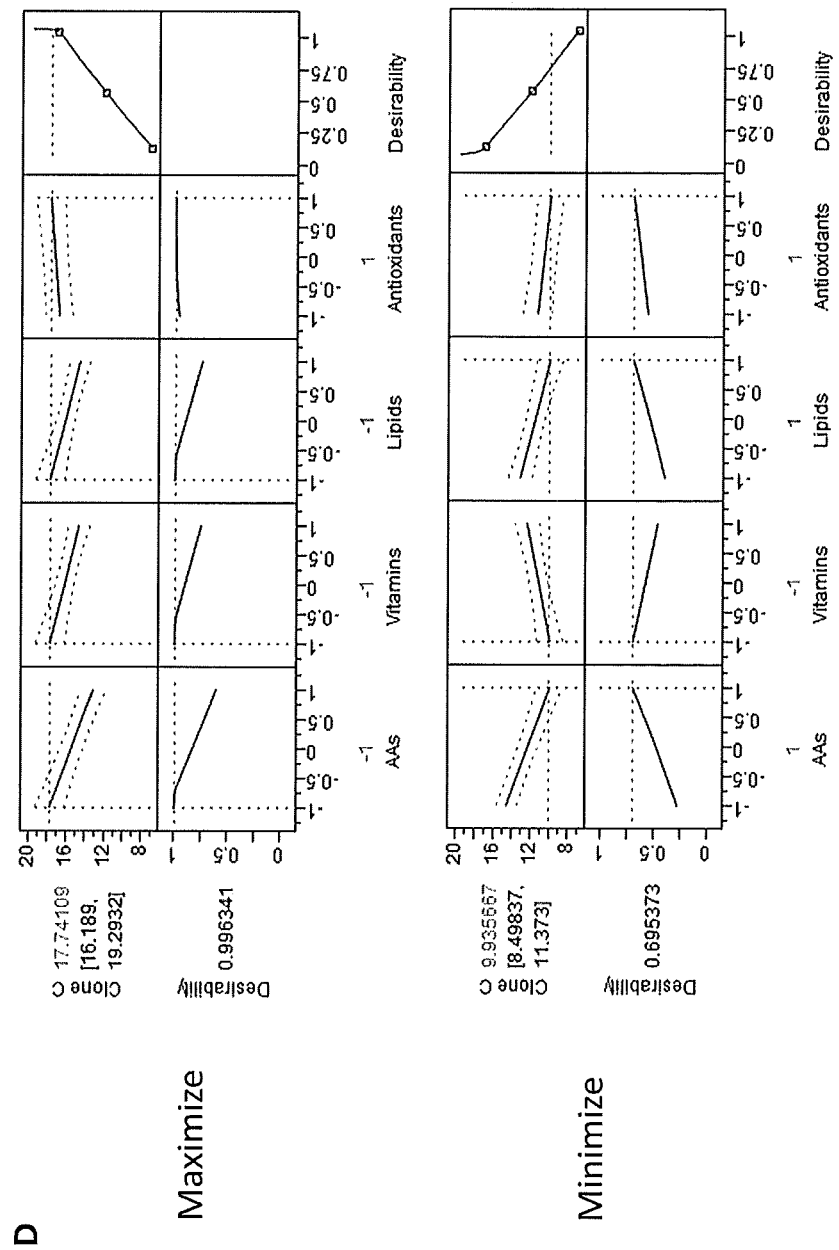
Figure 12:
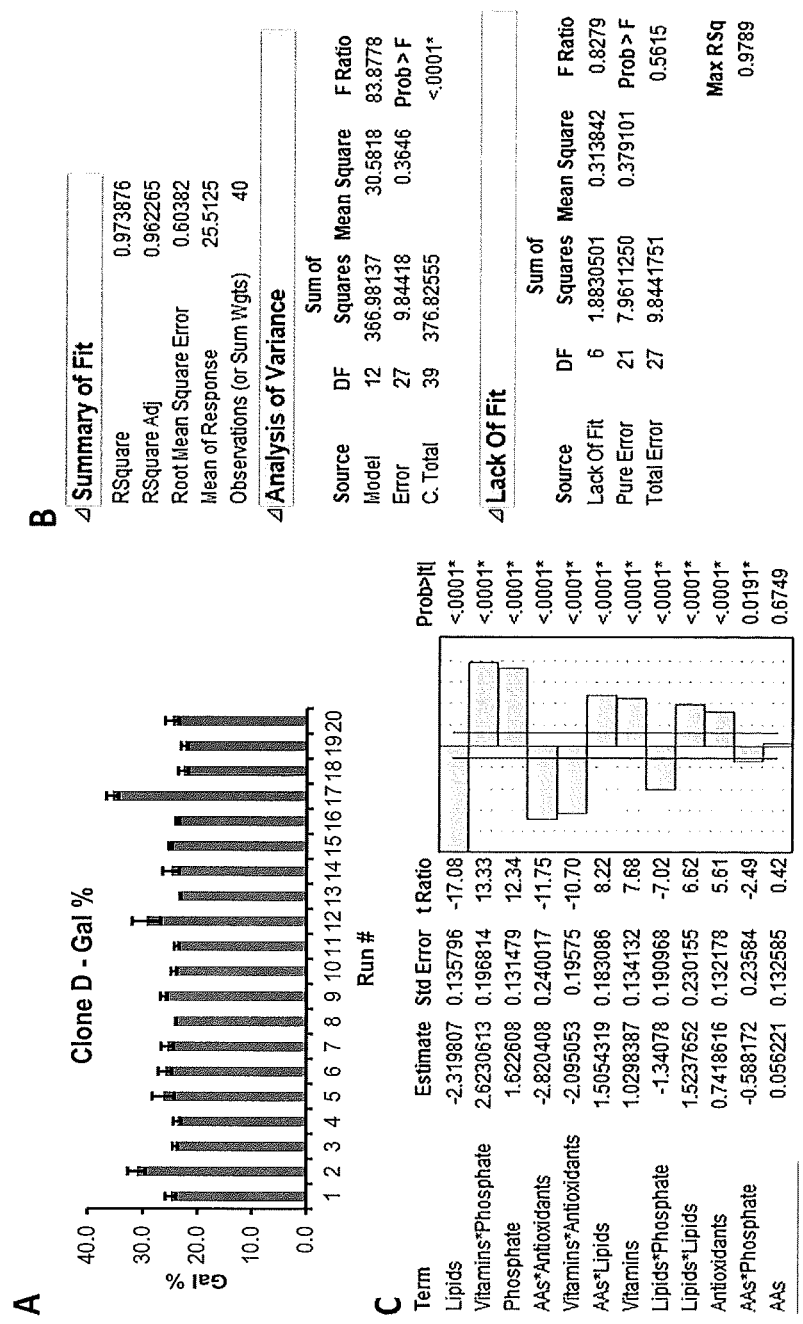
FIG. 12A-FIG. 12D show the statistical analysis of gal % for clone D. A: the levels of gal % for proteins produced from cells cultured in the prototype media. B: statistical summary for the mathematical model generated to fit the data shown in A. C: List of the major effects of the factors on gal % and the terms incorporated into the mathematical model. D: predicted maximum or minimum gal % levels using the model generated
Figure 12:
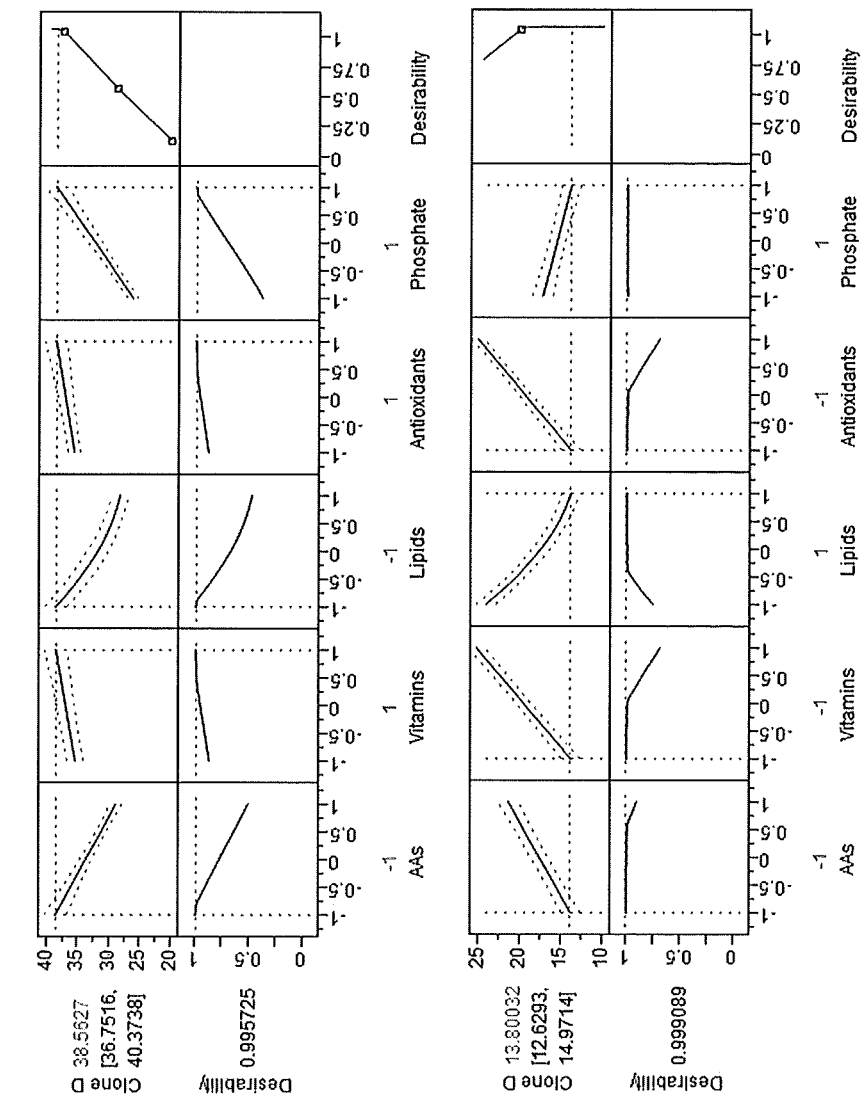
Figure 13:
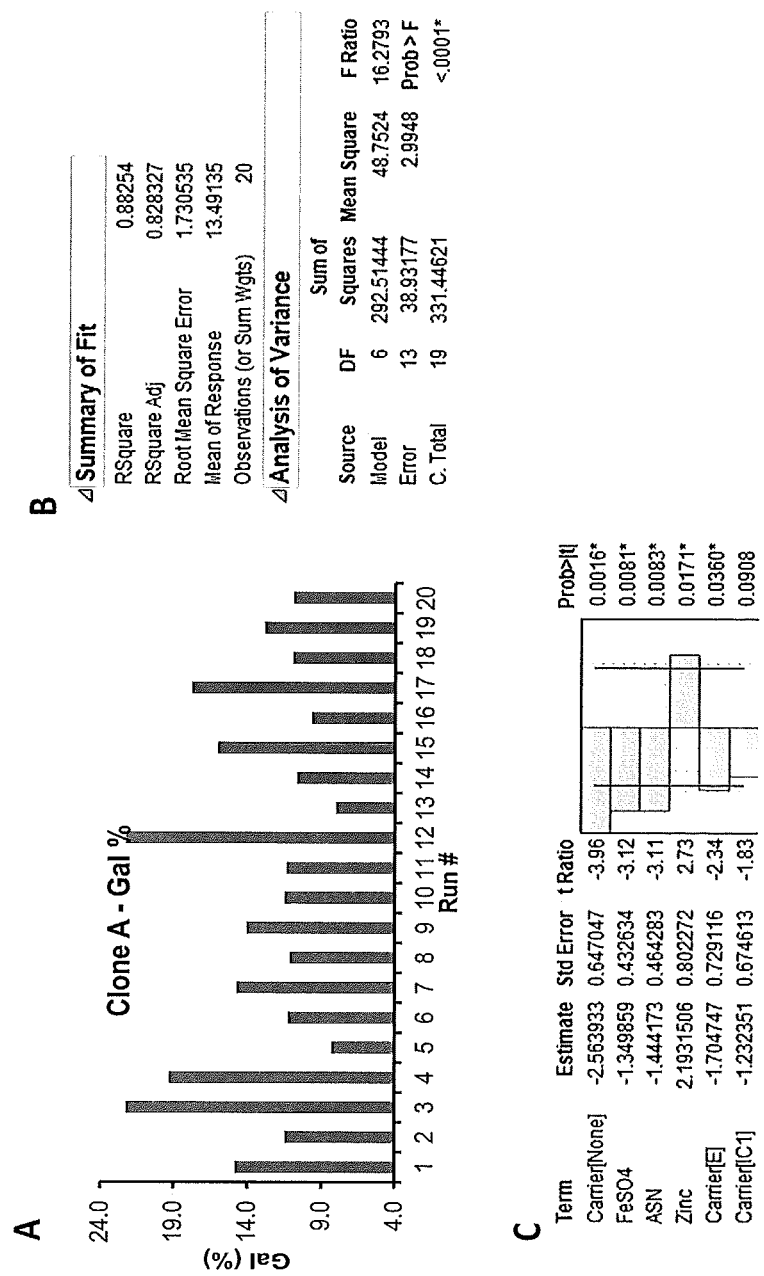
FIG. 13A-FIG. 13D show the statistical analysis of gal % for clone A. 13A: the levels of gal % for proteins produced from cells cultured in the prototype media. 13B: statistical summary for the mathematical model generated to fit the data shown in 13A. 13C: List of the major effects of the factors on gal % and the terms incorporated into the mathematical model. 13D: predicted maximum or minimum gal % levels using the model generated
Figure 13:
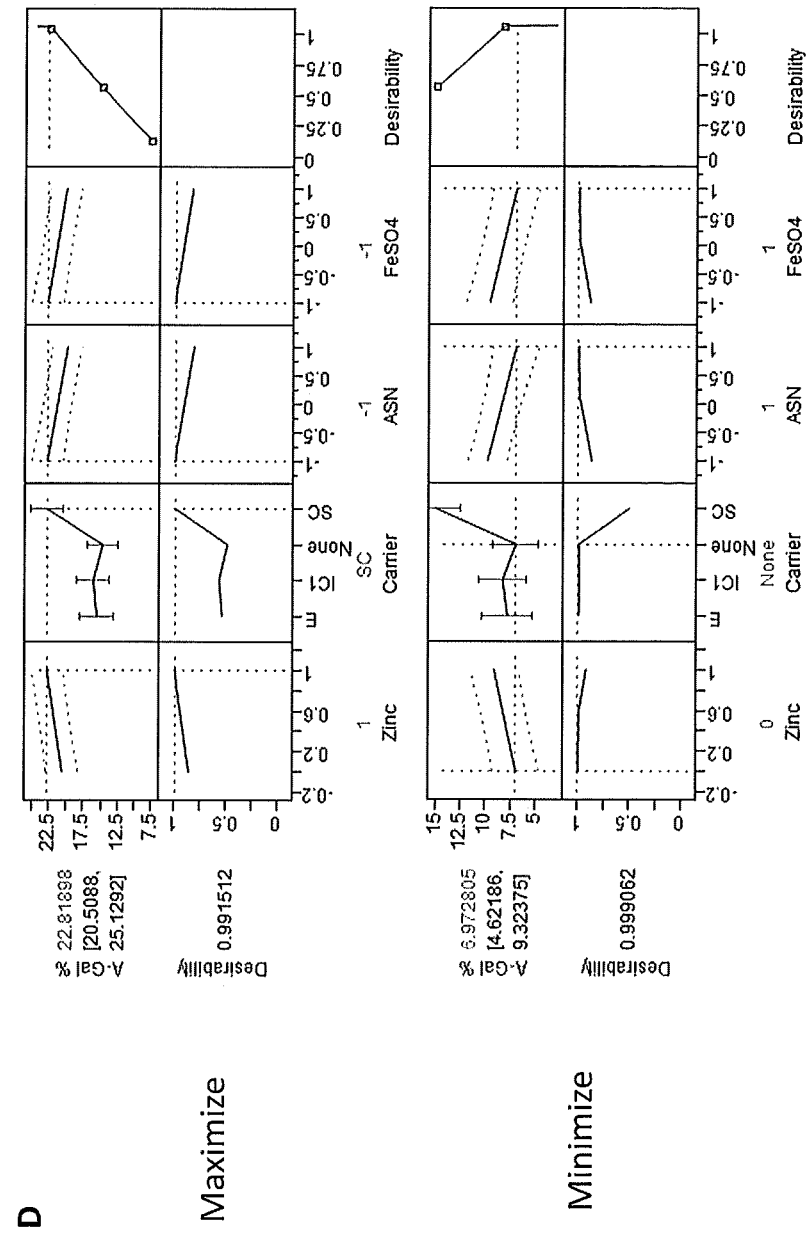
Figure 14:
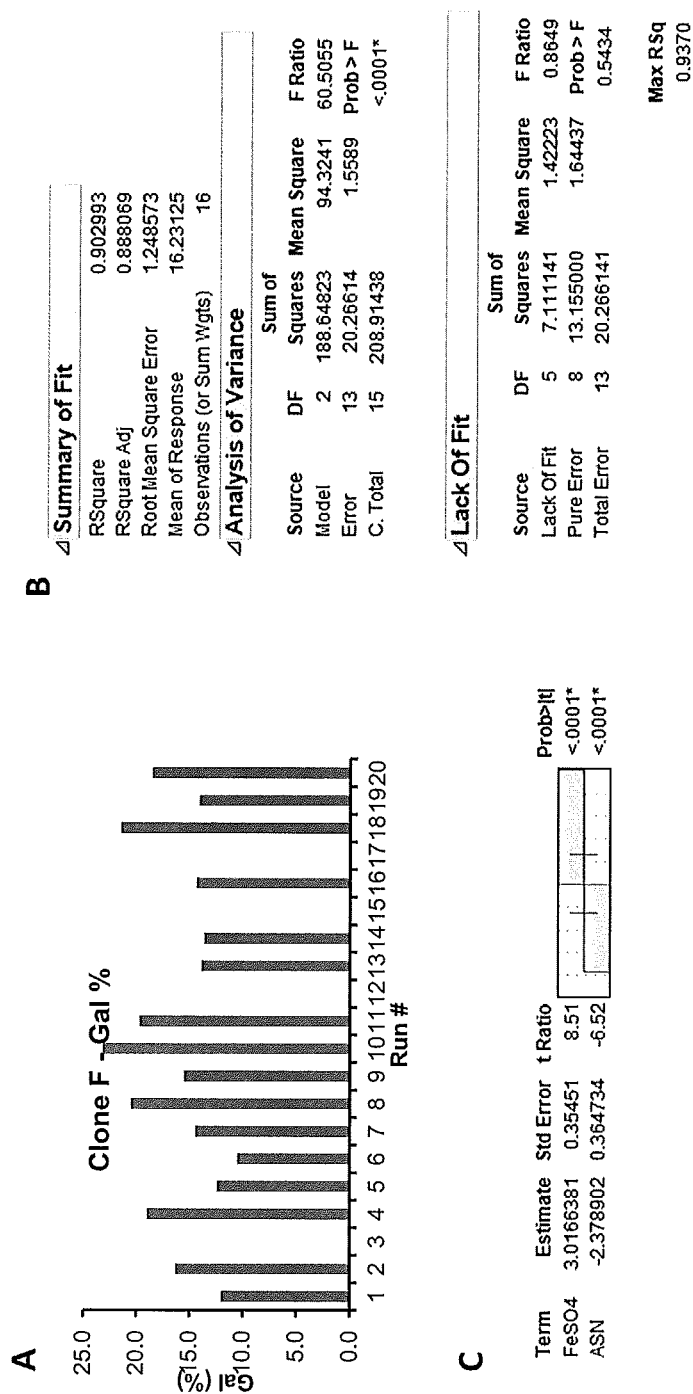
FIG. 14A-FIG. 14D show the statistical analysis of gal % for clone F. 14A: the levels of gal % for proteins produced from cells cultured in the prototype media. 14B: statistical summary for the mathematical model generated to fit the data shown in 14A. 14C: List of the major effects of the factors on gal % and the terms incorporated into the mathematical model. 14D: predicted maximum or minimum gal % levels using the model generated
Figure 14:
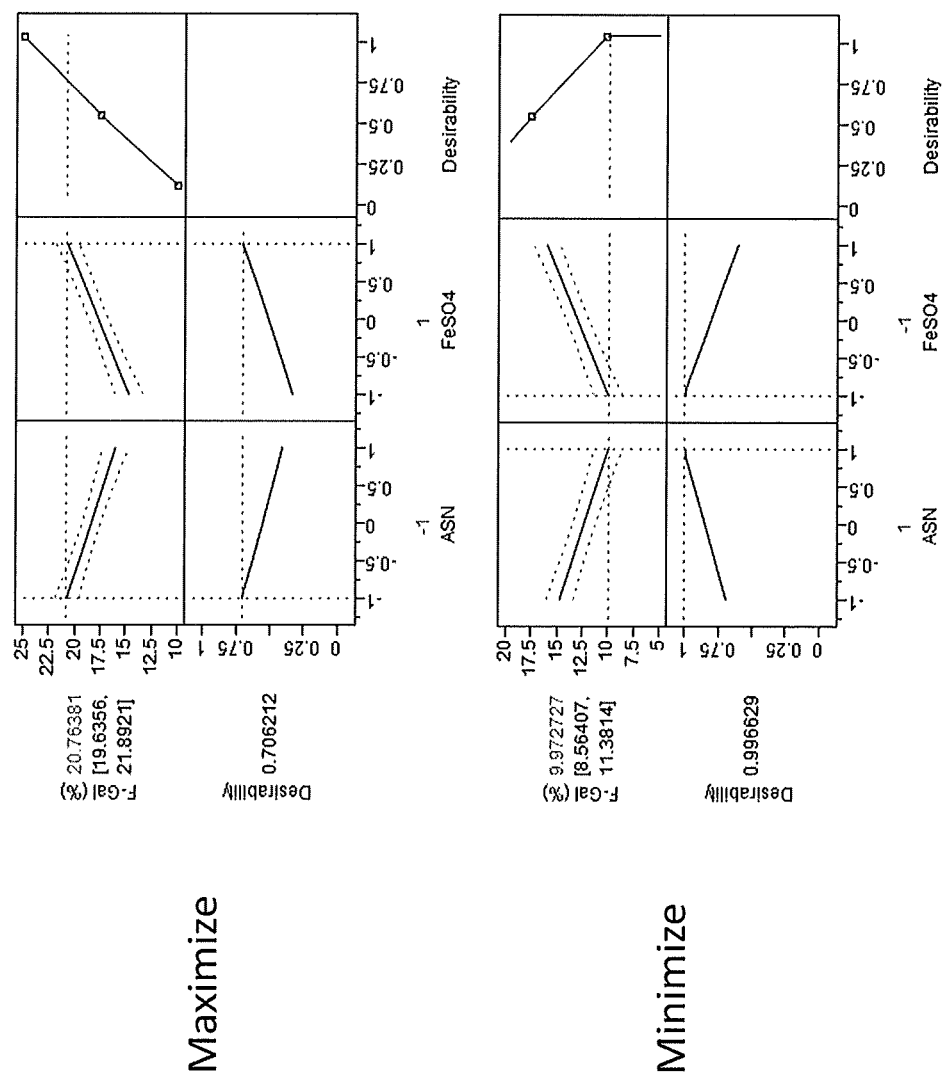
Figure 15:
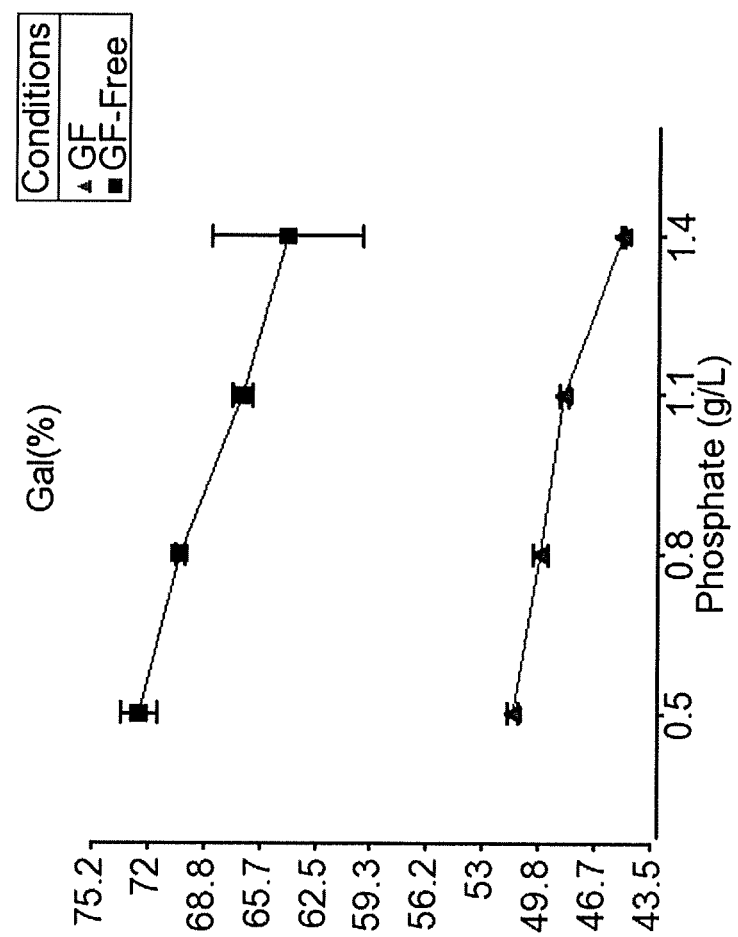
FIG. 15 shows the effect of growth factors and phosphate on gal % for clone B. Cells were cultured in the presence or absence of growth factors with varied concentration of phosphate. Note that gal % for GF-Free conditions were higher than that for GF conditions regardless of the phosphate concentration. Phosphate decreased the gal % for either GF or GF-free conditions. GF: growth factor; GF-free: growth factor free.
Figure 16:
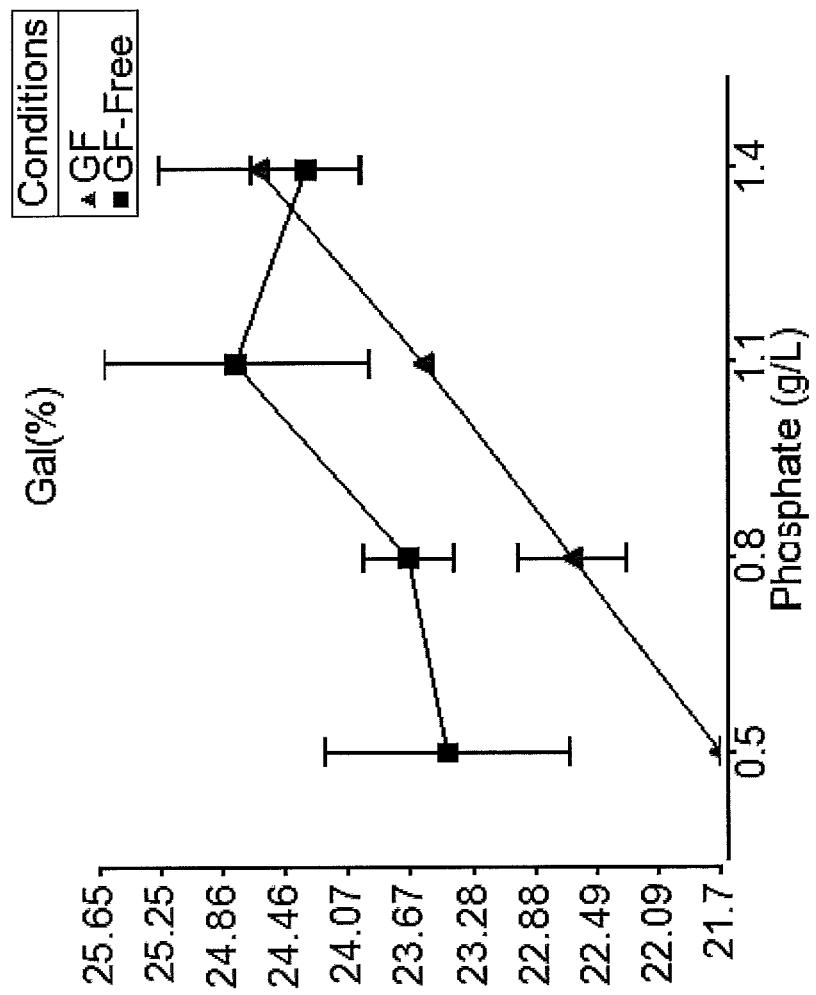
FIG. 16 shows the effect of growth factors and phosphate on gal % for clone G. Cells were cultured in the presence or absence of growth factors with varied concentration of phosphate. Note that gal % for GF-Free conditions were higher than that for GF conditions when phosphate concentration was below 1.1 g/L. Increase Phosphate from 0.5 to 1.1 g/L elevated the gal % for GF-free conditions; similarly, increase phosphate from 0.5 to 1.4 g/L led to higher gal % for GF conditions. GF: growth factor; GF-free: growth factor free.
Figure 17:
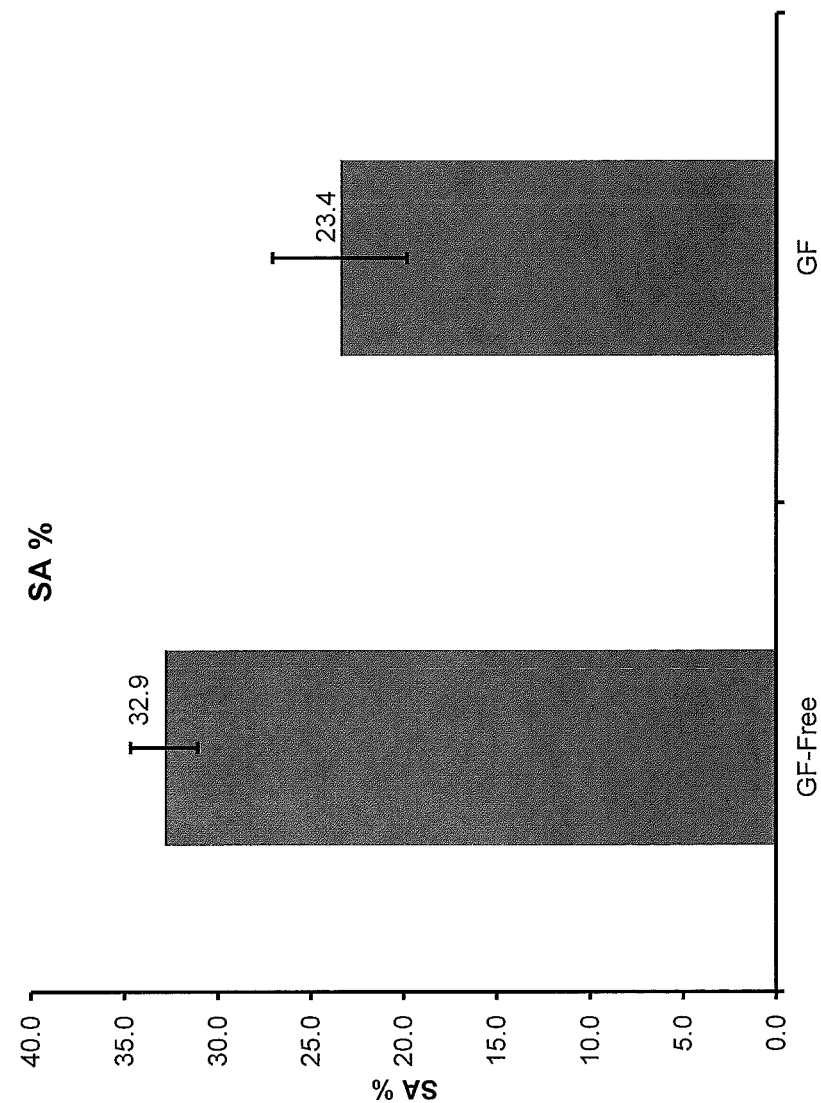
FIG. 17 shows clone B cultured in the presence of growth factor (1 mg/L insulin) resulted in lower SA % compared to the cultures without. GF: growth factor; GF-Free: growth factor free
Figure 18:
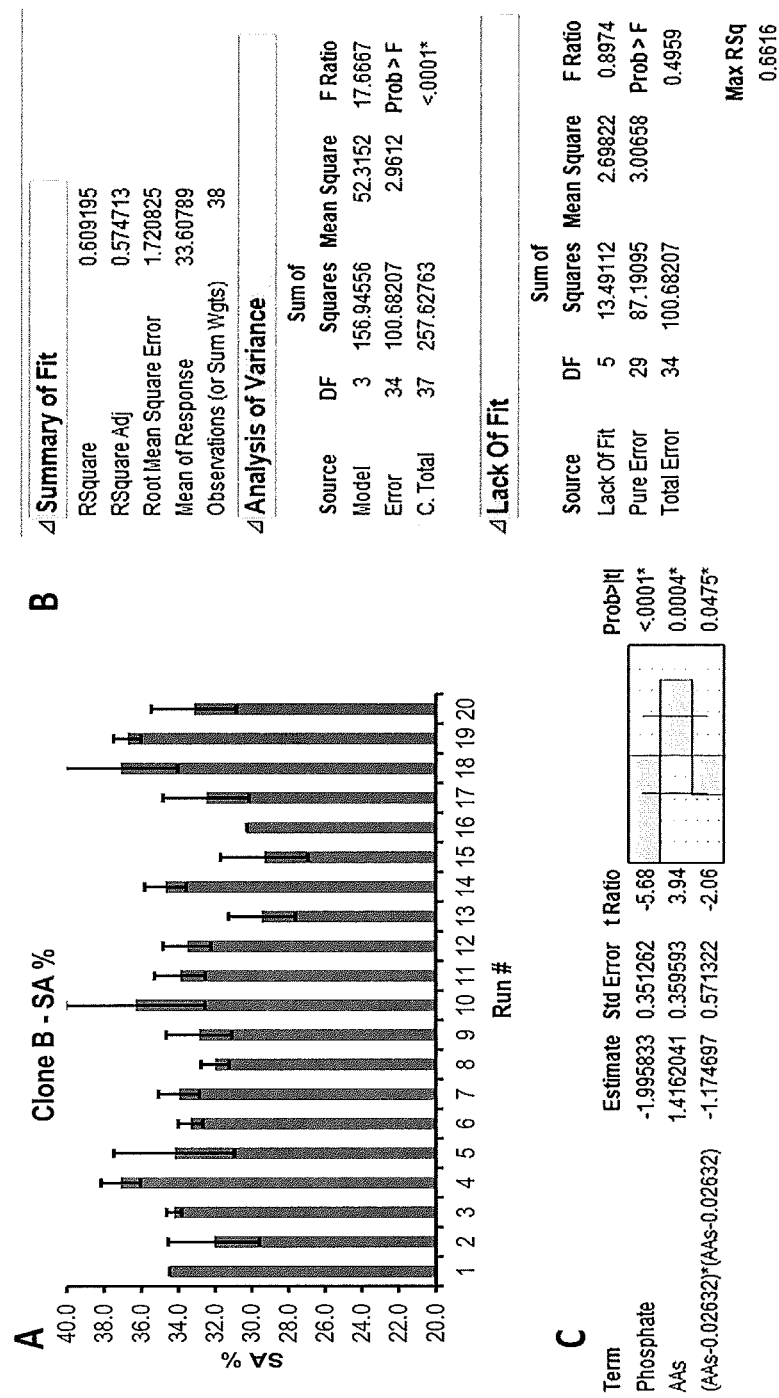
FIG. 18A-FIG. 18D show the statistical analysis of SA % for clone B. 18A: the levels of SA % for proteins produced from cells cultured in the prototype media. 18B: statistical summary for the mathematical model generated to fit the data shown in 18A. 18C: List of the major effects of the factors on SA % and the terms incorporated into the mathematical model. 18D: predicted maximum or minimum SA % levels using the model generated
Figure 18:
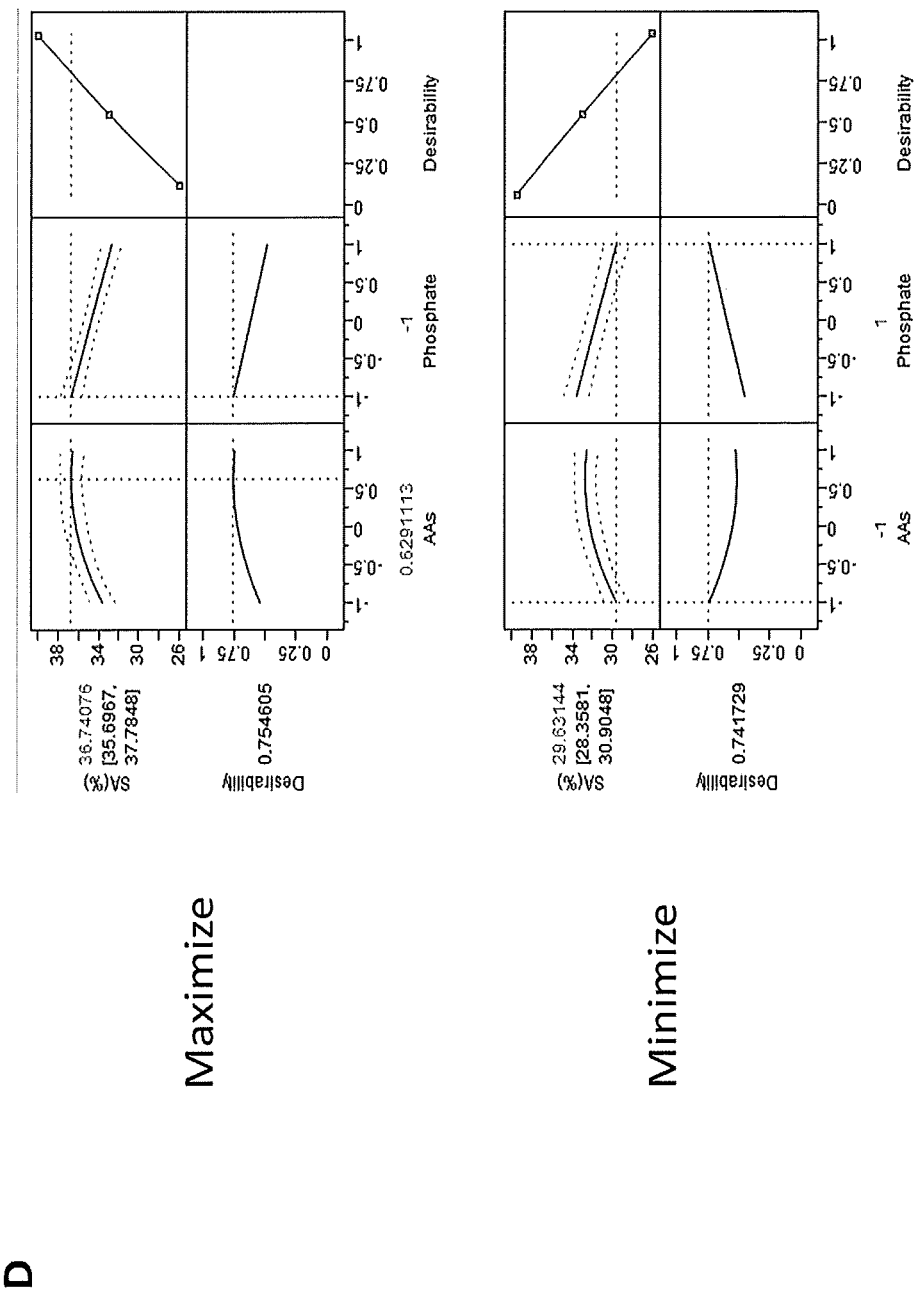
Figure 19:
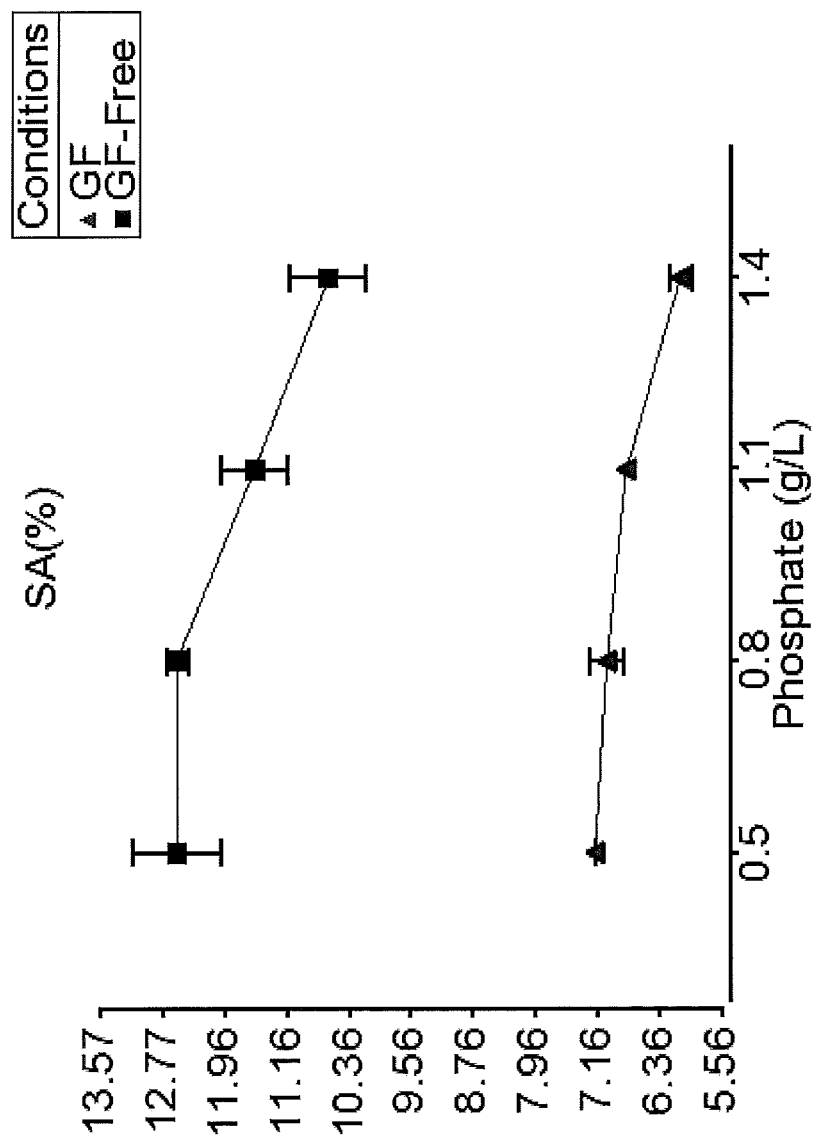
FIG. 19 shows the effect of growth factors and phosphate on SA % for clone B. Cells were cultured in the presence or absence of growth factors with varied concentration of phosphate. Note that SA % for GF-Free conditions were higher than that for GF conditions regardless of the phosphate concentration. Phosphate decreased the SA % for both GF and GF-free conditions. GF: growth factor; GF-free: growth factor free.
Figure 20:
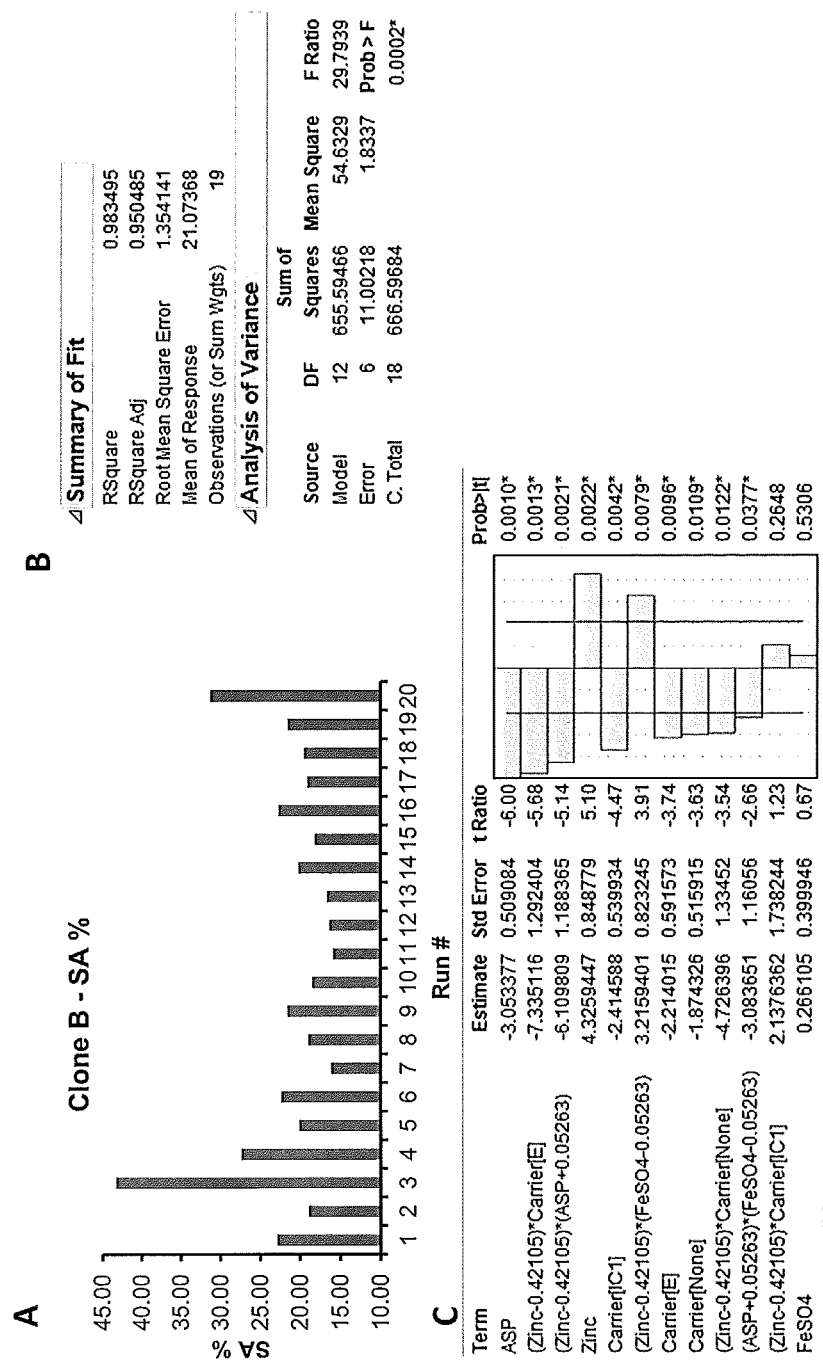
FIG. 20A-FIG. 20D show the statistical analysis of SA % for clone B. 20A: the levels of SA % for proteins produced from cells cultured in the prototype media. 20B: statistical summary for the mathematical model generated to fit the data shown in 20A. 20C: List of the major effects of the factors on SA % and the terms incorporated into the mathematical model. 20D: predicted maximum or minimum SA % levels using the model generated
Figure 20:
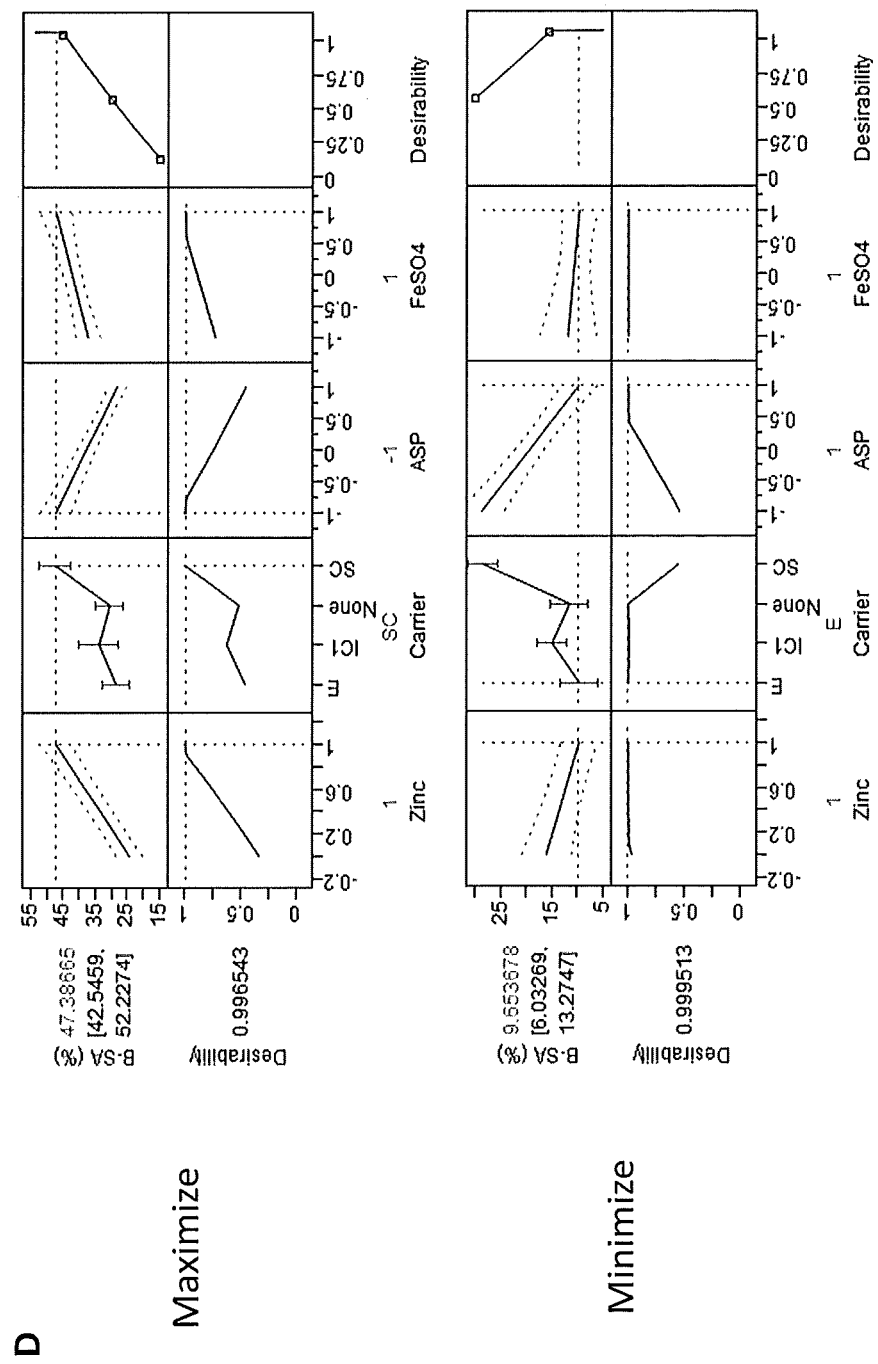
Figure 21:
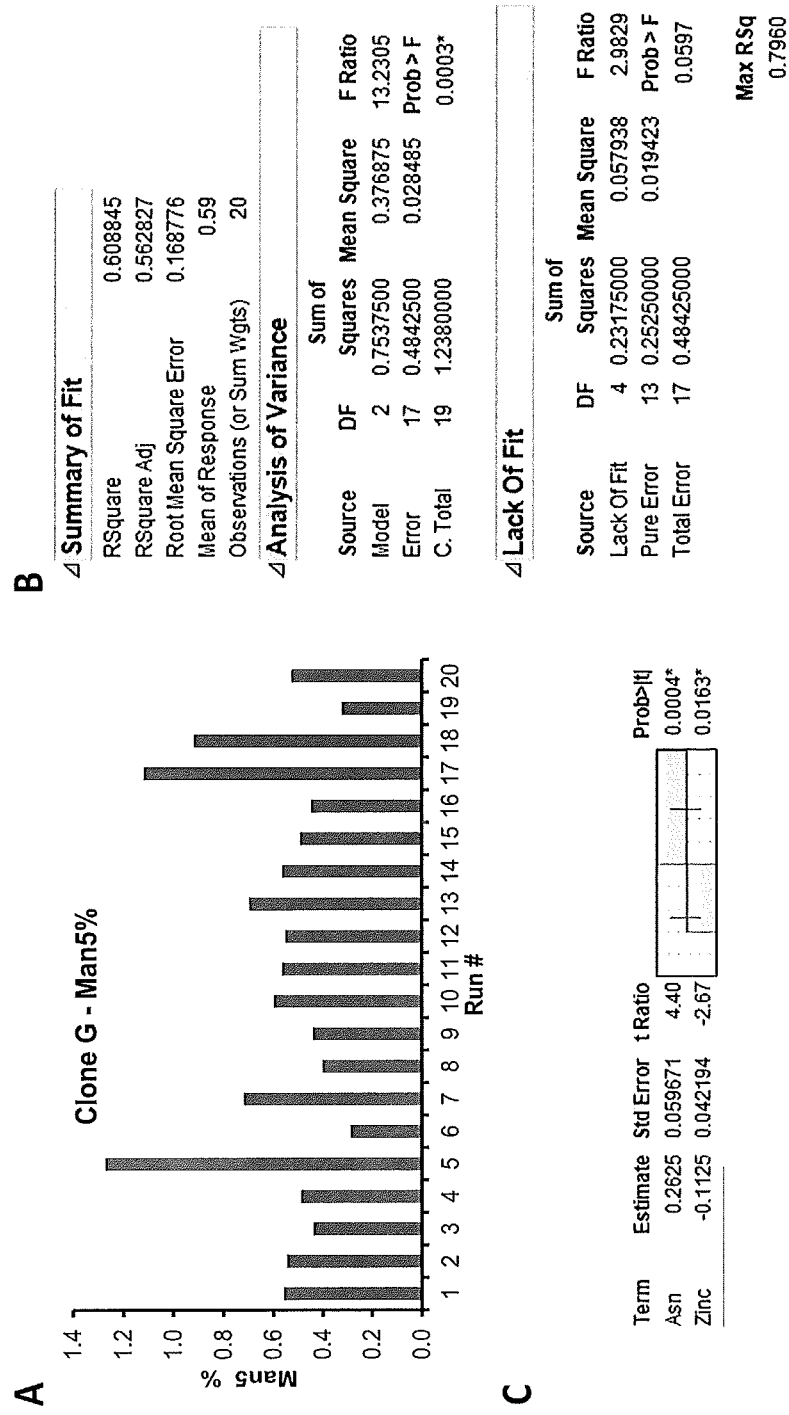
FIG. 21A-FIG. 21D show the statistical analysis of man5% for clone G. 21A: the levels of man5% for proteins produced from cells cultured in the prototype media. 21B: statistical summary for the mathematical model generated to fit the data shown in 21A. 21C: List of the major effects of the factors on man5% and the terms incorporated into the mathematical model. 21D: predicted maximum or minimum man5% levels using the model generated
Figure 21:
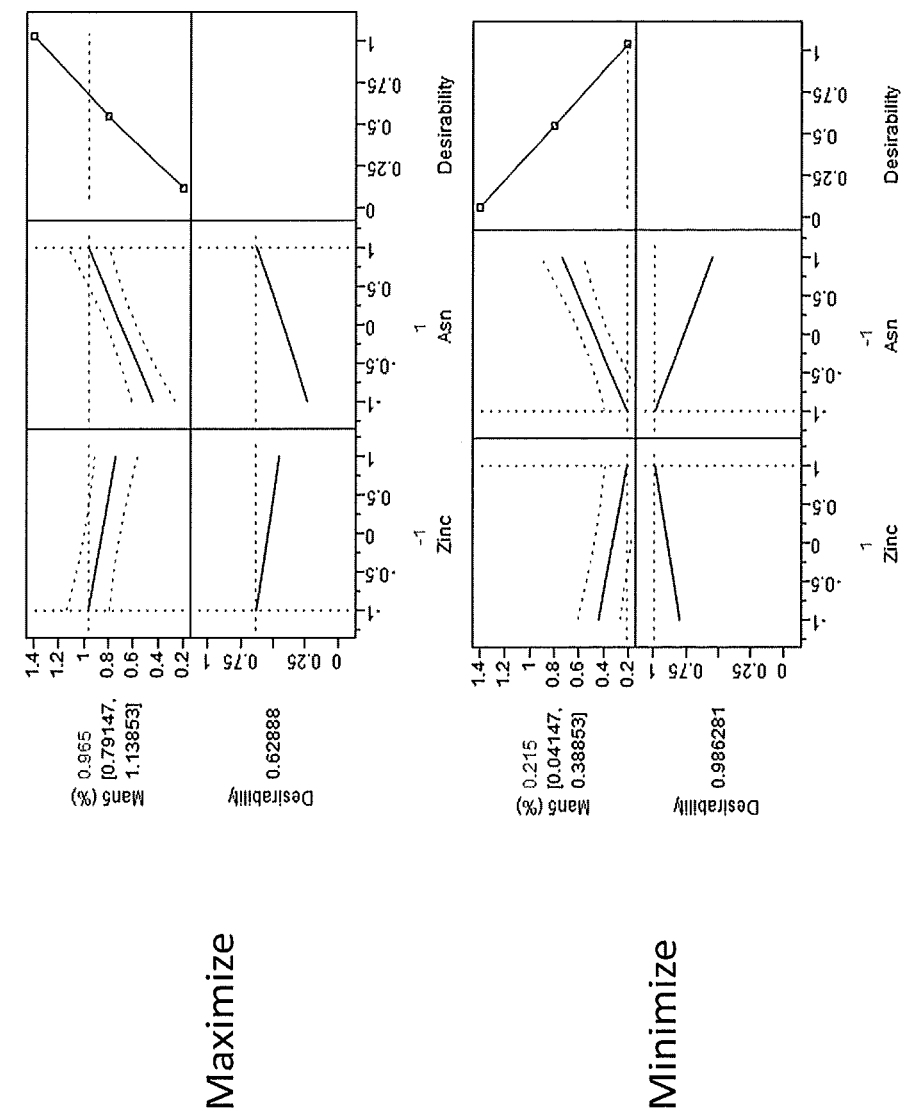
Figure 22:
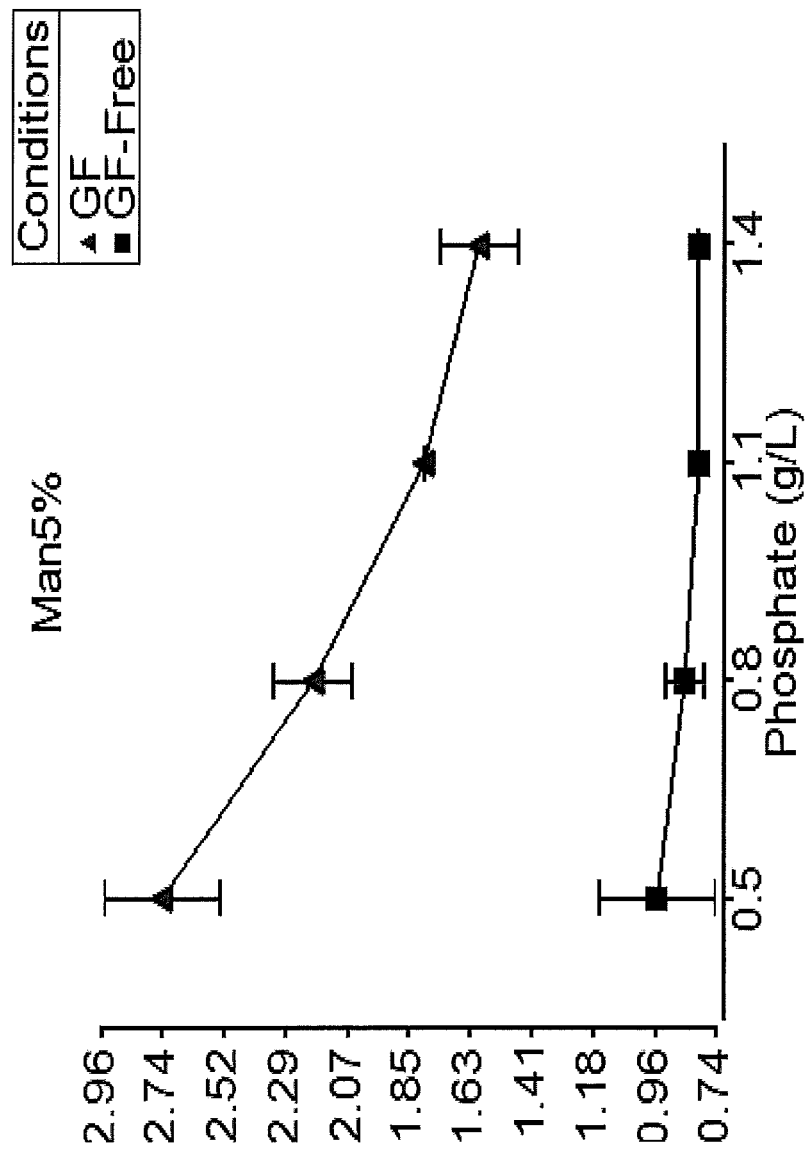
FIG. 22 shows the effect of growth factors and phosphate on man5% for clone G. Cells were cultured in the presence or absence of growth factors with varied concentration of phosphate. Note that man5% for GF-Free conditions were lower than that for GF conditions regardless of the phosphate concentration. Phosphate decreased the man5% for both GF and GF-free conditions. GF: growth factor; GF-free: growth factor free.
Figure 23:
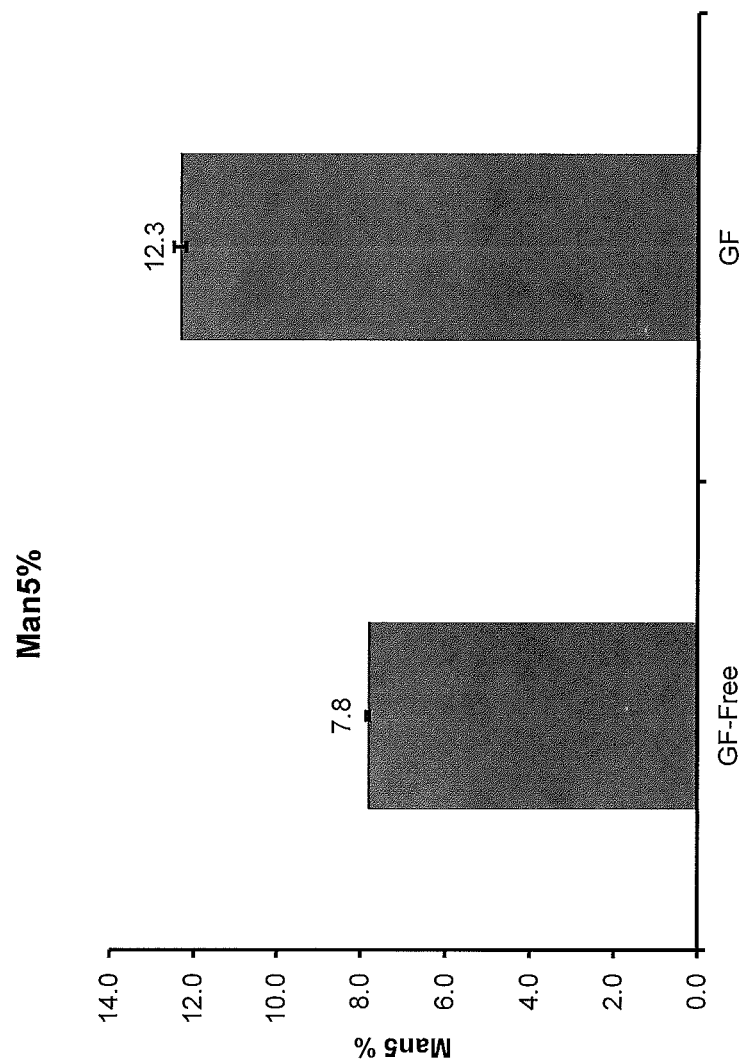
FIG. 23 shows that growth factor (1 mg/L insulin) decreased man5% for clone D. GF: growth factor; GF-free: growth factor free

| FIG. 7 Effect of Combined Factors on Gal % | | | | | | |
|---|---|---|---|---|---|---|
| | | Prediction Gal % | | Concentration Levels | | |
| Clone | Target | Level [Range] | Zn | Asn | FeSO4 | Iron Carrier | Asp |
| A | Max | 22.82 [20.51, 25.13] | 1 | −1 | −1 | SC | |
| | Min | 6.97 [4.62, 9.32] | 0 | 1 | 1 | None | |
| B | Max | 115.60 [103.91, 127.29] | 1 | | | SC | |
| | Min | 74.75 [63.06, 86.44] | 1 | | | E | |
| F | Max | 20.76 [19.64, 21.89] | | −1 | 1 | | |
| | Min | 9.97 [8.56, 11.38] | | 1 | −1 | | |

In the case of clone A, the Gal % level could be maximized at a mean value of 22.82% when zinc, Asn and FeSO4 were controlled at 1, −1, −1, respectively, with a 95% chance the Gal % will be in the range of 20.51 to 25.13%. However, if the levels for zinc, Asn, and FeSO4 are not properly set, the Gal % could decrease to as low as 4.62%.

In the case of clone F, the Gal % level could be maximized at a mean value of 20.76% when Asn and FeSO4 were controlled at −1, 1, respectively, with a 95% chance the Gal % will be in the range of 19.64 to 21.98. However, if the levels for Asn and FeSO4 are not properly set, the Gal % could decrease to as low as 8.562%.

Factors Impacting SA %

Table 8 below summarizes the effects of a single factor on percent sialic acid (SA %) in clone B.

TABLE 8

| Effect of Single Factor on SA % | | | | | | | | | | |
|---|---|---|---|---|---|---|---|---|---|---|
| Clone | Amino Acids | Phosphate | Lipids | Antioxidants | Vitamins | FeSO4 | Zn | Asn | Asp | Growth Factors |
| B | ↑ | ↓ | NE | NE | NE | NE | ↑ | NE | ↓ | ↓ |

NE: No Effect

While the addition of amino acids and zinc generally increased (↑) the SA %, the addition of phosphate, Asp and growth factors generally decreased (↓) SA %.

Table 9 below summarizes the combined factors that have an effect on SA % in clone B. The predictions are based on relative ranges: −1 is the lower range, 0 is the middle, and +1 is the higher range. All of the ranges are relative to the components in the media formulation.

TABLE 9

Effect of Combined Factors on SA %

| | | | Concentration Levels | | | | |
|---|---|---|---|---|---|---|---|
| Clone | Target | Prediction SA % Level [Range] | Amino Acids | Phosphate | Lipids | Antioxidants | Vitamins |
| B | Max | 36.74 [35.70, 37.78] | 0.63 | −1 | | | |
| | Min | 29.63 [28.36, 30.90] | −1 | 1 | | | |

In the case of clone B, the SA % level could be maximized at a mean value of 36.74% with a 95% chance the SA % will be in the range of 35.70 to 37.78%. However, if the levels for amino acids or phosphate are not properly set, the SA % could decrease to as low as 28.36%.

Table 10 below summarizes the effects specific ingredients have on SA % in clone B.

TABLE 10

Effect of Combined Factors on SA %

| | | | | | | Concentration Levels | | |
|---|---|---|---|---|---|---|---|---|
| Clone | Target | Prediction SA % Level [Range] | Zn | Asn | FeSO4 | Iron Carrier | Asp |
| B | Max | 47.39 [42.55, 52.23] | 1 | | 1 | SC | −1 |
| | Min | 9.65 [6.03, 13.27] | 1 | | 1 | E | 1 |

In the case of clone B, the SA % level could be maximized at a mean value of 47.39% when Asp was controlled at −1, with a 95% chance the SA % will be in the range of 42.55 to 52.23%. However, if the level of Asp is not properly set, the SA % could decrease to as low as 6.03%.

Factors Impacting Man5%

Table 11 below summarizes the effects of a single factor on percent mannose 5 (Man5%) in clones D and G. While the addition of asparagine or growth factors generally increased (↑) the Man5%, the addition of phosphate or zinc generally decreased (↓) Man5%.

TABLE 11

Effect of Single Factor on Man5%

| Clone | Amino Acids | Phosphate | Lipids | Antioxidants | Vitamins | FeSO4 | Zn | Asn | Growth Factors |
|---|---|---|---|---|---|---|---|---|---|
| D | NE | NE | NE | NE | NE | NE | NE | NE | ↑ |
| G | NE | ↓ | NE | NE | NE | NE | ↓ | ↑ | ↑ |

NE: No Effect

Cells, Proteins and Cell Culture

In the cell culture processes or methods of this invention, the cells can be maintained in a variety of cell culture media. i.e., basal culture media, as conventionally known in the art. For example, the methods are applicable for use with large volumes of cells maintained in cell culture medium, which can be supplemented with nutrients and the like. Typically, "cell culturing medium" (also called "culture medium") is a term that is understood by the practitioner in the art and is known to refer to a nutrient solution in which cells, preferably animal or mammalian cells, are grown and which generally provides at least one or more components from the following: an energy source (usually in the form of a carbohydrate such as glucose); all essential amino acids, and generally the twenty basic amino acids, plus cysteine; vitamins and/or other organic compounds typically required at low concentrations; lipids or free fatty acids, e.g., linoleic acid; and trace elements, e.g., inorganic compounds or naturally occurring elements that are typically required at very low concentrations, usually in the micromolar range. Cell culture medium can also be supplemented to contain a variety of optional components, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal protein (peptone or peptone mixtures, which can be obtained from animal byproducts, purified gelatin or plant material); antibiotics, e.g., gentamycin; and cell protective agents, e.g., a Pluronic polyol (Pluronic F68). Preferred is a cell nutrition medium that is serum-free and free of products or ingredients of animal origin, and chemically defined.

As is appreciated by the practitioner, animal or mammalian cells are cultured in a medium suitable for the particular cells being cultured and which can be determined by the person of skill in the art without undue experimentation. Commercially available media can be utilized and include, for example, Minimal Essential Medium (MEM, Sigma, St. Louis, Mo.); Ham's F10 Medium (Sigma); Dulbecco's Modified Eagles Medium (DMEM, Sigma); RPMI-1640 Medium (Sigma); HyClone cell culture medium (HyClone, Logan, Utah); and chemically-defined (CD) media, which are formulated for particular cell types. To the foregoing, exemplary media can be added the above-described supplementary components or ingredients, including optional components, in appropriate concentrations or amounts, as necessary or desired, and as would be known and practiced by those having in the art using routine skill.

In addition, cell culture conditions suitable for the methods of the present invention are those that are typically employed and known for batch, fed-batch, or continuous culturing of cells, with attention paid to pH (e.g., about 6.5 to about 7.5), dissolved oxygen ($O_2$) (e.g., between about 5-90% of air saturation), carbon dioxide ($CO_2$) (e.g., between about 10-150 mmHg), agitation (between about 50 to 200 rpm) and humidity, in addition to temperature (between about 30° C. to 37° C.). As an illustrative, yet nonlimiting, example, a suitable cell culturing medium for the fed-batch processes of the present invention comprises a chemically defined basal and feed medium, preferably one or both containing the antioxidants of the invention (e.g., Example 1).

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or growth factors. Growth factors and nutrients that are necessary for the growth and maintenance of particular cell cultures are able to be readily determined empirically by those having skill in the pertinent art, such as is described, for example, by Barnes and Sato, (1980, *Cell*, 22:649); in *Mammalian Cell Culture*, Ed. J. P. Mather, Plenum Press, N Y, 1984; and in U.S. Pat. No. 5,721,121.

Numerous types of cells can be cultured according to the methods of the present invention. The cells are typically animal or mammalian cells that can express and secrete, or that can be molecularly engineered to express and secrete, large quantities of a particular protein into the culture medium. It will be understood that the protein produced by a host cell can be endogenous or homologous to the host cell. Alternatively, and preferably, the protein is heterologous, i.e., foreign, to the host cell, for example, a human protein produced and secreted by a Chinese hamster ovary (CHO) host cell.

Examples of mammalian proteins that can be advantageously produced by the methods of this invention include, without limitation, cytokines, cytokine receptors, growth factors (e.g., EGF, HER-2, FGF-α, FGF-β, TGF-α, TGF-β, PDGF. IGF-1, IGF-2, NGF, NGF-β); growth factor receptors, including fusion or chimeric proteins. Other nonlimiting examples include growth hormones (e.g., human growth hormone, bovine growth hormone); insulin (e.g., insulin A chain and insulin B chain), proinsulin; erythropoietin (EPO); colony stimulating factors (e.g., G-CSF, GM-CSF, M-CSF); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; follicle stimulating hormone (FSH); luteinizing hormone (LH); calcitonin; CD proteins (e.g., CD3, CD4, CD8, CD28, CD19, etc.); CTLA proteins (e.g., CTLA4); T-cell and B-cell receptor proteins; bone morphogenic proteins (BNPs, e.g., BMP-1, BMP-2, BMP-3, etc.); neurotrophic factors, e.g., bone derived neurotrophic factor (BDNF); neurotrophins, e.g., 3-6; refill; rheumatoid factor; RANTES; albumin; relaxin; macrophage inhibitory protein (e.g., MIP-1, MIP-2); viral proteins or antigens; surface membrane proteins; ion channel proteins; enzymes; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art. Fusion proteins and polypeptides, chimeric proteins and polypeptides, as well as fragments or portions, or mutants, variants, or analogs of any of the aforementioned proteins and polypeptides are also included among the suitable proteins, polypeptides and peptides that can be produced by the methods of the present invention.

Nonlimiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, *Som. Cell Molec. Genet.*, 12:555-556; Kolkekar et al., 1997, *Biochemistry*, 36:10901-10909; and WO 01/92337 A2), dihydrofolate reductase negative CHO cells (CHO/-DHFR, Urlaub and Chasin, 1980, *Proc. Natl. Acad. Sci. USA*, 77:4216), and dp12.CHO cells (U.S. Pat. No. 5,721,121). Preferred are CHO cells, particularly, recombinant CHO cell lines established with DHFR or GS gene expression systems.

The cells suitable for culturing in the methods and processes of the present invention can contain introduced (e.g., via transformation, transfection, infection, or injection) expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

Control elements, or regulatory sequences, are those non-translated regions of the vector (e.g., enhancers, promoters, 5' and 3' untranslated regions) that interact with host cellular proteins to carry out transcription and translation. Such elements can vary in their strength and specificity. Depending on the vector system and host cell utilized, any number of suitable transcription and translation elements, including constitutive and inducible promoters, can be used. In mammalian cell systems, promoters from mammalian genes or from mammalian viruses are preferred. The constructs for use in protein expression systems are designed to contain at least one promoter, an enhancer sequence (optional, for mammalian expression systems), and other sequences as necessary or required for proper transcription and regulation of gene expression (e.g., transcriptional initiation and termination sequences, origin of replication sites, polyadenylation sequences, e.g., the Bovine Growth Hormone (BGH) poly A sequence).

As will be appreciated by those skilled in the art, the selection of the appropriate vector, components for proper transcription, expression, and isolation of proteins produced in eukaryotic expression systems is known and routinely determined and practiced by those having skill in the art. The expression of proteins by the cells cultured in accordance with the methods of this invention can be placed under the control of promoters such as viral promoters, e.g., cytomegalovirus (CMV), Rous sarcoma virus (RSV), phosphoglycerol kinase (PGK), thymidine kinase (TK), or the α-actin promoter. Further, regulated promoters confer inducibility by particular compounds or molecules, e.g., the glucocorticoid response element (GRE) of mouse mammary tumor virus (MMTV) is induced by glucocorticoids (V. Chandler et al., 1983, *Cell*, 33:489-499). Also, tissue-specific promoters or regulatory elements can be used (G. Swift, et al., 1984, *Cell*, 38:639-646), if necessary or desired.

Expression constructs can be introduced into cells by a variety of gene transfer methods known to those skilled in the art, for example, conventional gene transfection methods, such as calcium phosphate co-precipitation, liposomal transfection, microinjection, electroporation, and infection or viral transduction. The choice of the method is within the competence of the skilled practitioner in the art. It will be apparent to those skilled in the art that one or more constructs carrying DNA sequences for expression in cells can be transfected into the cells such that expression products are subsequently produced in and/or obtained from the cells.

In a particular aspect, mammalian expression systems containing appropriate control and regulatory sequences are preferred for use in protein expressing mammalian cells of the present invention. Commonly used eukaryotic control sequences for generating mammalian expression vectors include promoters and control sequences compatible with mammalian cells such as, for example, the cytomegalovirus (CMV) promoter (CDM8 vector) and avian sarcoma virus (ASV) πLN vector. Other commonly used promoters include the early and late promoters from Simian Virus 40 (SV40) (Fiers et al., 1973, *Nature*, 273:113), or other viral promoters such as those derived from polyoma, Adenovirus 2, and bovine papilloma virus. An inducible promoter, such as hMTII (Karin et al., 1982, *Nature*, 299:797-802) can also be used.

Examples of expression vectors suitable for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene), retroviral vectors (e.g., pFB vectors (Stratagene)), pcDNA-3 (Invitrogen), adenoviral vectors; Adeno-associated virus vectors, baculovirus vectors, yeast vectors (e.g., pESC vectors (Stratagene)), or modified forms of any of the foregoing. Vectors can also contain enhancer sequences upstream or downstream of promoter region sequences for optimizing gene expression.

A selectable marker can also be used in a recombinant vector (e.g., a plasmid) to confer resistance to the cells harboring (preferably, having stably integrated) the vector to allow their selection in appropriate selection medium. A number of selection systems can be used, including but not limited to, the Herpes Simplex Virus thymidine kinase (HSV TK), (Wigler et al., 1977, *Cell*, 11:223), hypoxanthine-guanine phosphoribosyltransferase (HGPRT), (Szybalska and Szybalski, 1992, *Proc. Natl. Acad. Sci. USA*, 48:202), and adenine phosphoribosyltransferase (Lowy et al., 1980, *Cell*, 22:817) genes, which can be employed in tk-, hgprt-, or aprt-cells (APRT), respectively.

Anti-metabolite resistance can also be used as the basis of selection for the following nonlimiting examples of marker genes: dhfr, which confers resistance to methotrexate (Wigler et al., 1980, *Proc. Natl. Acad. Sci. USA*, 77:357; and O'Hare et al., 1981, *Proc. Natl. Acad. Sci. USA*, 78:1527); gpt, which confers resistance to mycophenolic acid (Mulligan and Berg, 1981, *Proc. Natl. Acad. Sci. USA*, 78:2072); neo, which confers resistance to the aminoglycoside G418 (*Clinical Pharmacy*, 12:488-505; Wu and Wu, 1991, *Biotherapy*, 3:87-95; Tolstoshev, 1993, *Ann. Rev. Pharmacol. Toxicol.*, 32:573-596; Mulligan, 1993, *Science*, 260:926-932; Anderson, 1993, *Ann. Rev. Biochem.*, 62:191-21; May, 1993, *TIB TECH*, 11(5):155-215; and hygro, which confers resistance to hygromycin (Santerre et al., 1984, *Gene*, 30:147). Methods commonly known in the art of recombinant DNA technology can be routinely applied to select the desired recombinant cell clones, and such methods are described, for example, in Ausubel et al. (eds.), *Current Protocols in Molecular Biology*, John Wiley & Sons, N Y (1993); Kriegler, 1990, Gene Transfer and Expression, *A Laboratory Manual*, Stockton Press, NY; in Chapters 12 and 13, Dracopoli et al. (eds), *Current Protocols in Human Genetics*, John Wiley & Sons, N Y (1994); Colberre-Garapin et al., 1981. *J. Mol. Biol.*, 150:1, which are incorporated by reference herein in their entireties.

In addition, the expression levels of an expressed protein molecule can be increased by vector amplification (for a review, see Bebbington and Hentschel, "The use of vectors based on gene amplification for the expression of cloned genes in mammalian cells in DNA cloning", Vol. 3, Academic Press, New York, 1987). When a marker in the vector system expressing a protein is amplifiable, an increase in the level of inhibitor present in the host cell culture will increase the number of copies of the marker gene. Since the amplified region is associated with the protein-encoding gene, production of the protein will concomitantly increase (Crouse et al., 1983, *Mol. Cell. Biol.*, 3:257).

Vectors which harbor glutamine synthase (GS) or dihydrofolate reductase (DHFR) encoding nucleic acid as the selectable markers can be amplified in the presence of the drugs methionine sulphoximine or methotrexate, respectively. An advantage of glutamine synthase based vectors is the availability of cell lines (e.g., the murine myeloma cell line, NSO) which are glutamine synthase negative. Glutamine synthase expression systems can also function in glutamine synthase expressing cells (e.g., CHO cells) by providing additional inhibitor to prevent the functioning of the endogenous gene.

Vectors that express DHFR as the selectable marker include, but are not limited to, the pSV2-dhfr plasmid (Subramani et al., *Mol. Cell. Biol.* 1:854 (1981). Vectors that express glutamine synthase as the selectable marker include, but are not limited to, the pEE6 expression vector described in Stephens and Cockett, 1989, *Nucl. Acids. Res.*, 17:7110. A glutamine synthase expression system and components thereof are detailed in PCT publications: WO87/04462; WO86/05807; WO89/01036; WO89/10404; and WO91/06657 which are incorporated by reference herein in their entireties. In addition, glutamine synthase expression vectors that can be used in accordance with the present invention are commercially available from suppliers, including, for example, Lonza Biologics, Inc. (Portsmouth, N.H.).

Types of Cell Culture

For the purposes of understanding, yet without limitation, it will be appreciated by the skilled practitioner that cell cultures and culturing runs for protein production can include three general types; namely, continuous culture, batch culture and fed-batch culture. In a continuous culture, for example, fresh culture medium supplement (i.e., feeding medium) is provided to the cells during the culturing period, while old culture medium is removed daily and the product is harvested, for example, daily or continuously. In continuous culture, feeding medium can be added daily and can be added continuously, i.e., as a drip or infusion. For continuous culturing, the cells can remain in culture as long as is desired, so long as the cells remain alive and the environmental and culturing conditions are maintained.

In batch culture, cells are initially cultured in medium and this medium is neither removed, replaced, nor supplemented, i.e., the cells are not "fed" with new medium, during or before the end of the culturing run. The desired product is harvested at the end of the culturing run.

For fed-batch cultures, the culturing run time is increased by supplementing the culture medium one or more times daily (or continuously) with fresh medium during the run, i.e., the cells are "fed" with new medium ("feeding medium") during the culturing period. Fed-batch cultures can include the various feeding regimens and times, for example, daily, every other day, every two days, etc., more than once per day, or less than once per day, and so on. Further, fed-batch cultures can be fed continuously with feeding medium. The desired product is then harvested at the end of the culturing/production run.

CHO Clones

MDX1100 (Clone A)

In another embodiment, the CHO-K1 cells were transfected with a GS gene expression system in order to establish a stable cell line expressing a human IgG4 antibody.

The transfected and cloned cells expressing the antibody was grown in media with varied concentrations of the tested factors according to the methods of the invention. [see example 2 to 5]

The antibody produced by clone A is described in U.S. application 2005/0191293, which is incorporated herein by reference.

Myostatin (Clone G)

In another embodiment, the dhfr-negative Chinese Hamster Ovary (CHO) cell line DG44 was transfected in order to establish a stable cell line expressing a recombinant human fusion protein.

The transfected and cloned CHO DG44 cells expressing the fusion protein was grown in media with varied concentrations of the tested factors according to the methods of the invention. [see examples 2 to 5]

The fusion protein produced by clone G is described in U.S. Pat. No. 8,933,199, which is incorporated herein by reference.

aCD40L (Clone B)

In another embodiment, the dhfr-negative Chinese Hamster Ovary (CHO) cell line DG44 was transfected in order to establish a stable cell line expressing a recombinant human fusion protein.

The transfected and cloned CHO DG44 cells expressing the antibody was grown in media with varied concentrations of the tested factors according to the methods of the invention. [see examples 2 to 5]

The antibody produced by clone B is described in U.S. Pat. No. 8,895,010, which is incorporated herein by reference.

aLag 3 (Clone C)

In another embodiment, the dhfr-negative Chinese Hamster Ovary (CHO) cell line DG44 was transfected in order to establish a stable cell line expressing a human IgG4 antibody.

The transfected and cloned CHO DG44 cells expressing the antibody was grown in media with varied concentrations of the tested factors according to the methods of the invention. [see Examples 2 to 5]

The antibody produced by clone C is described in PCT application WO2014/008218, which is incorporated herein by reference.

MDX1110 (Clone D)

In another embodiment, the dhfr-negative Chinese Hamster Ovary (CHO) cell line CHO-Ms704 were transfected in order to establish a stable cell line expressing a human IgG4 antibody.

The transfected and cloned cells expressing the antibody was grown in media with varied concentrations of the tested factors according to the methods of the invention. [see examples 2 to 5]

The antibody produced by clone D is described in U.S. Pat. No. 8,383,118, which is incorporated herein by reference.

aKir (Clone F)

In another embodiment, the CHO-K1 cells were transfected with a GS gene expression system in order to establish a stable cell line expressing a human IgG4 antibody.

The transfected and cloned cells expressing the antibody was grown in media with varied concentrations of the tested factors according to the methods of the invention. [see examples 2 to 5]

The antibody produced by clone F is described in PCT application WO2008/084106, which is incorporated herein by reference.

Pharmaceutical Formulations

In certain embodiments, produced polypeptides will have pharmacologic activity and will be useful in the preparation of pharmaceuticals. Inventive compositions as described above may be administered to a subject or may first be formulated for delivery by any available route including, but not limited to parenteral, intravenous, intramuscular, intradermal, subcutaneous, oral, buccal, sublingual, nasal, bronchial, opthalmic, transdermal (topical), transmucosal, rectal, and vaginal routes. Inventive pharmaceutical compositions typically include a purified polypeptide expressed from a mammalian cell line, a delivery agent in combination with a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into compositions of the present invention. For example, a polypeptide produced according to the present invention may be conjugated to drugs for systemic pharmacotherapy, such as toxins, low-molecular-weight cytotoxic drugs, biological response modifiers, and radionuclides (see e.g., Kunz et al., Calicheamicin derivative-carrier conjugates, US20040082764 A1). Additional ingredients useful in preparing pharmaceutical compositions in accordance with the present invention include, for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Alternatively or additionally, a polypeptide produced according to the present invention may be administered in combination with (whether simultaneously or sequentially) one or more additional pharmaceutically active agents. An exemplary list of these pharmaceutically active agents can be found in the Physicians' Desk Reference, 55 Edition, published by Medical Economics Co., Inc., Montvale, N.J., 2001, incorporated herein by reference in its entirety. For many of these listed agents, pharmaceutically effective dosages and regimens are known in the art; many are presented in the Physicians' Desk Reference itself.

Solid pharmaceutical compositions may contain one or more solid carriers, and optionally one or more other additives such as flavoring agents, lubricants, solubilizers, suspending agents, fillers, glidants, compression aids, binders or tablet-disintegrating agents or an encapsulating material. suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier may be a finely divided solid which is in admixture with the finely divided active ingredient. In tablets, the active ingredient is generally mixed with a carrier having the necessary compression properties in suitable proportions, and optionally, other additives, and compacted into the desired shape and size.

Liquid pharmaceutical compositions may contain the polypeptide expressed according to the present invention and one or more liquid carriers to form solutions, suspensions, emulsions, syrups, elixirs, or pressurized compositions. Pharmaceutically acceptable liquid carriers include, for example water, organic solvents, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of, or limit the amount of, alcohol.

Examples of liquid carriers suitable for oral or parenteral administration include water (optionally containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for, example by, intramuscular, intraperitoneal, epidural, intrathecal, intravenous or subcutaneous injection. Pharmaceutical compositions for oral or transmucosal administration may be either in liquid or solid composition form.

In certain embodiments, a pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Advantageously, certain pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain cases, it will be useful to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide in the required amount in an appropriate solvent with one or a combination of ingredients enumerated above, as required, followed by filtered sterilization. Generally, dispersions are prepared by incorporating the purified polypeptide expressed from a mammalian cell line into a sterile vehicle which contains a basic dispersion medium and the required other ingredients from those enumerated above. In the case of sterile powders for the preparation of sterile injectable solutions, advantageous methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide can be incorporated with excipients and used in the form of tablets, troches, or capsules, e.g., gelatin capsules. Oral compositions can also be prepared using a fluid carrier, e.g., for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Such preparations may be mixed chewable or liquid formulations or food materials or liquids if desirable, for example to facilitate administration to children, to individuals whose ability to swallow tablets is compromised, or to animals. Formulations for oral delivery may advantageously incorporate agents to improve stability within the gastrointestinal tract and/or to enhance absorption.

Alternatively, the compounds can be administered in the form of a suppository or pessary, or they may be applied topically in the form of a gel, hydrogel, lotion or other glycerides, solution, cream, ointment or dusting powder.

In some embodiments, compositions are prepared with carriers that will protect the polypeptide against rapid elimination from the body, such as a controlled release formulation, including implants and microencapsulated delivery systems. In general, inventive compositions may be formulated for immediate, delayed, modified, sustained, pulsed, or controlled-release delivery. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Suitable materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, pharmaceutical compositions of the present invention are provided in unit dosage form, such as tablets or capsules. It may be advantageous to formulate oral or parenteral compositions in unit dosage form for ease of administration and uniformity of dosage. In such form, the composition is sub-divided in unit dose containing appropriate quantities of the polypeptide. The unit dosage forms can be packaged compositions, for example packeted powders, vials, ampoules, pre-filled syringes or sachets containing liquids. As one skilled in the art will recognize, therapeutically effective unit dosage will depend on several factors, including, for example, the method of administration, the potency of the polypeptide, and/or the weight of the recipient and the identities of other components in the pharmaceutical composition.

A polypeptide expressed according to the present invention can be administered at various intervals and over different periods of time as required, e.g., daily, weekly, biweekly, monthly, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a polypeptide as described herein may comprise a single treatment or a series of treatments. It is furthermore understood that appropriate doses may depend upon the potency of the polypeptide and may optionally be tailored to the particular recipient, for example, through administration of increasing doses until a preselected desired response is achieved. It is understood that the specific dose level for any particular animal subject may depend upon a variety of factors including the activity of the specific polypeptide employed, the age, body weight, general health, gender, and diet of the subject, the time of administration, the route of administration, the rate of excretion, any drug combination, and the degree of expression or activity to be modulated.

Inventive pharmaceutical compositions can be included in a container, pack, or dispenser together with instructions for administration.

Example 1

Experiment Procedures: a vial of frozen cells were thawed into BMS proprietary basal medium 17I with or without growth factors (see details for each individual experiment) and cultured for 3 passages. The cells were then transferred to modified 17I prototype media with different treatments with increased or decreased concentration of nutrient components (see details for each individual experiment). The cells were adapted in the prototype media for 3 passages prior to setting up batch cultures in order to evaluate the performance of the prototype media. On days 12 of the fed-batch culture, supernatant samples were harvested and purified with proA Chromatography columns. The purified protein samples were then subjected to protein quality attribute analyses (see FIG. 1). Cell culture parameters: cells were cultured either in 50 ml spin tubes with an initial volume of 25 ml and a shaking speed of 300 rpm or 500 ml shaker flasks with an initial volume of 150 ml and a shaking speed of 150 rpm on an orbital shaker with 25 mm throw distance. Temperature for the culture was controlled at 37° C. and CO2 was controlled at 6%. Cells were cultured in spin tubes for Experiment 2, and in shaker flasks for the rest of the experiments.

High molecule weight analyses: high molecular weight species were analyzed with size exclusion HPLC with a Tosoh Bioscience TSKgel SuperSW3000 column and SuperSW guard column, and an aqueous buffered mobile phase.

Glycosylation profile analyses: intact mass analysis with LC-MS was used to compare the glycosylation profiles of protein samples. About 0.5 μg of each protein sample was loaded onto a Poros reversed phase 2.1×100 mm column (Applied Biosystems, Foster City, Calif.) equilibrated with 0.1% formic acid in 20% (v/v) acetonitrile and separated by a gradient elution from 20% to 50% acetonitrile with 0.1% formic acid in 25 min, at a flow rate of 0.25 mL/min. Eluent was electrosprayed into a Q-ToF Ultima mass spectrometer (Waters, Milford, Mass.) for online detection. The mass spectra were combined and deconvoluted using MaxEnt1 algorithm (Waters, Milford, Mass.). Peaks were assigned at 100 ppm mass accuracy.

Statistical Analysis: Customized factorial (fractional or response surface depending on the levels studied for each factor) Design of Experiment (DOE) was used to generate the run conditions using statistical software JMP® 10.0.0 (SAS Institute Inc.). Each response (e.g., HMW %, Gal %, etc) was analyzed using the stepwise regression method with minimum AICc, minimum BIC, or p-value threshold stopping rules. Only when p-values were less than 0.05 were the terms selected to generate a mathematical model with standard least squares method. The model was then used to analyze the impact of the factors on the responses and to predict the max or min value for each response.

Example 2

Basal medium 17I was modified with the components listed in Table 1. Except for the lipids group, the concentration for each component was shown as a percentage increase or decrease to the existing concentration for the component in 17I. The specific component and concentration for the lipids group is proprietary to Hyclone. The modified components were grouped into amino acids, vitamins, lipids, antioxidants, and phosphate based on the functions or properties for the chemical compounds. The groups were then the study factors used to generate prototype media conditions shown in table 12 using a response surface statistical design approach. Cells were cultured in the prototype media without any growth factors following the protocol described in Example 1 above. In addition, cells were also cultured in prototype medium #9 with a growth factor (1 mg/L insulin) and served as a control to compare the impact of growth factors on the protein quality attributes.

TABLE 12

| Run # | AAs | Vitamins | Lipids | Antioxidants | Phosphate |
|---|---|---|---|---|---|
| 1 | 0 | 0 | 0 | 1 | 0 |
| 2 | 1 | 1 | 1 | −1 | 0 |
| 3 | 0 | 0 | 0 | 0 | 0 |
| 4 | 1 | 0 | 1 | 1 | −1 |
| 5 | 1 | −1 | −1 | −1 | 1 |
| 6 | −1 | 1 | −1 | 1 | −1 |
| 7 | 0 | 0 | 0 | 0 | 0 |
| 8 | 0 | 0 | 1 | 0 | 1 |

TABLE 12-continued

| Run # | AAs | Vitamins | Lipids | Antioxidants | Phosphate |
|---|---|---|---|---|---|
| 9 | −1 | 0 | −1 | −1 | 0 |
| 10 | 1 | 0 | −1 | 0 | −1 |
| 11 | −1 | −1 | 0 | 0 | −1 |
| 12 | 0 | −1 | −1 | 1 | 0 |
| 13 | −1 | 0 | 0 | −1 | 1 |
| 14 | 1 | −1 | 0 | 0 | 0 |
| 15 | −1 | −1 | 1 | 1 | 1 |
| 16 | −1 | 1 | 1 | 0 | 0 |
| 17 | 0 | 1 | −1 | 0 | 1 |
| 18 | 0 | −1 | 1 | −1 | −1 |
| 19 | 0 | 1 | 0 | −1 | −1 |
| 20 | 1 | 1 | 0 | 1 | 1 |

Example 3

Experiment Description: Following the cell culture protocol described in Example 1 above, cells were cultured in 17I with different concentration of phosphate ranging from 0.5 to 1.4 g/L either in the presence or absence of growth factors (1 mg/L insulin) as described in Table 13 below.

TABLE 13

| Clone | Condition | Medium | Phosphate (g/L) |
|---|---|---|---|
| B | GF-Free | 17I | 0.5 |
|   |   |   | 0.8 |
|   |   |   | 1.1 |
|   |   |   | 1.4 |
|   | GF | 17I | 0.5 |
|   |   |   | 0.8 |
|   |   |   | 1.1 |
|   |   |   | 1.4 |
| G | GF-Free | 17I | 0.5 |
|   |   |   | 0.8 |
|   |   |   | 1.1 |
|   |   |   | 1.4 |
|   | GF | 17I | 0.5 |
|   |   |   | 0.8 |
|   |   |   | 1.1 |
|   |   |   | 1.4 |

Example 4

Experiment Description: The initial media for this experiment was basal medium 17I with additional amino acids, antioxidants, and phosphate at level "+1" (see Table 1). The medium was then modified for the single component or group of components listed in Table 14 below.

TABLE 14

| Group | Components | Level 1 (Coded) | Level 2 (Coded) | Level 3 (Coded) | Concentration Range |
|---|---|---|---|---|---|
| Zinc | Zinc | 0 (−1) | +50% (0) | +100% (+1) | 0.01-100 mg/L |
| FeSO4 | FeSO4 | 0 (0) | −50% (−1) | −70% (−2) | 0.01-100 mg/L |
| Iron Carrier | E | | N/A | | 0.01-1 g/L |
| | IC1 | | | | 0.01-1 g/L |
| | IC2 | | | | 0.01-1 g/L |
| | None | | | | N/A |
| Vitamins | Folic Acid (B9) | 0 (0) | −50% (−1) | NA | 0.01-100 mg/L |
| | Cyanochobalamin (B12) | 0 (0) | −50% (−1) | NA | 0.01-100 mg/L |
| | Riboflavin (B2) | 0 (0) | −50% (−1) | NA | 0.01-100 mg/L |
| L-Asparagine | L-Asparagine | 0 (−1) | +50% (0) | +100% (+1) | 0.1-2 g/L |

The groups were then the study factors used to generate prototype media conditions shown in Table 15 using a customized statistical Design of Experiment (DoE) approach. Cells were cultured in the prototype media without any growth factors following the protocol described in Example 1 above.

TABLE 15

| Run # | Zinc | Asn | FeSO4 | Iron Carrier | Colorant |
|---|---|---|---|---|---|
| 1 | −1 | 0 | 0 | E | 0 |
| 2 | 1 | 0 | −1 | E | 0 |
| 3 | 0 | 0 | −2 | E | 0 |
| 4 | 1 | 1 | 0 | none | 0 |
| 5 | −1 | 1 | −2 | none | 0 |
| 6 | 1 | −1 | 0 | IC1 | 0 |
| 7 | 0 | 0 | −1 | IC1 | 0 |
| 8 | −1 | −1 | −2 | IC1 | 0 |
| 9 | 0 | 0 | 0 | IC2 | 0 |
| 10 | −1 | 0 | −1 | IC2 | 0 |
| 11 | −1 | −1 | 0 | none | −1 |
| 12 | 1 | 0 | 0 | E | −1 |
| 13 | −1 | 0 | −1 | E | −1 |
| 14 | 1 | 0 | −2 | IC2 | −1 |
| 15 | 0 | 0 | −1 | none | −1 |
| 16 | 1 | −1 | −2 | none | −1 |
| 17 | −1 | 1 | 0 | IC1 | −1 |
| 18 | 1 | 1 | −2 | IC1 | −1 |
| 19 | 1 | 0 | −1 | IC2 | −1 |
| 20 | −1 | 0 | −2 | IC2 | −1 |

E: EDTA; none: no Fe Carrier;
IC1 & IC2: iron carrier proprietary to Hyclone at concentration 1 & 2

Example 5

Experiment Description: The initial media for this experiment was basal medium 17I with additional amino acids, antioxidants, and phosphate at level "+1" (see table 1). The medium was then modified for the single component or group of components listed in table 16 below.

TABLE 16

| Group | Components | Level 1 (Coded) | Level 2 (Coded) | Level 3 (Coded) | Concentration Range |
|---|---|---|---|---|---|
| Zinc | Zinc | 0 (0) | +50% (+1) | NA | 0.01-100 mg/L |
| FeSO4 | FeSO4 | −30% (−1) | 0 (0) | +50% (+1) | 0.01-100 mg/L |
| Iron Carrier | E | | N/A | | 0.01-1 g/L |
| | IC1 | | | | 0.01-1 g/L |
| | Sodium Citrate (SC) | | | | 0.01-1 g/L |
| | None | | | | N/A |
| L-Aspartic Acid | L-Aspartic Acid | 0 (−1) | +50% (0) | +100% (+1) | 0.1-2 g/L |
| L-Asparagine | L-Asparagine | 0 (−1) | +50% (0) | +100% (+1) | 0.1-2 g/L |

The groups were then the study factors used to generate prototype media conditions shown in Table 17 using a customized statistical Design of Experiment (DoE) approach. Cells were cultured in the prototype media without any growth factors following a protocol described in Example 1 above. E: EDTA; none: no Fe Carrier; IC1: iron carrier proprietary to Hyclone; SC: sodium citriate.

TABLE 17

| Run # | Zinc | Carrier | Asp | Asn | FeSO4 |
|---|---|---|---|---|---|
| 1 | 1 | IC1 | −1 | 0 | −1 |
| 2 | 0 | None | −1 | −1 | 0 |
| 3 | 1 | SC | −1 | 0 | 0 |
| 4 | 1 | SC | 1 | −1 | 1 |
| 5 | 0 | None | 1 | 1 | 0 |
| 6 | 0 | E | 0 | 1 | −1 |
| 7 | 1 | E | 0 | −1 | −1 |
| 8 | 0 | E | 0 | −1 | 1 |
| 9 | 0 | SC | 0 | 1 | 1 |
| 10 | 0 | None | 0 | −1 | 1 |
| 11 | 1 | IC1 | 1 | 0 | 1 |
| 12 | 1 | SC | 1 | 1 | −1 |
| 13 | 0 | IC1 | 0 | 1 | 0 |
| 14 | 1 | None | 0 | 0 | −1 |
| 15 | 0 | IC1 | 1 | −1 | −1 |
| 16 | 1 | E | 0 | 1 | 1 |
| 17 | 0 | SC | 0 | −1 | −1 |
| 18 | 0 | IC1 | −1 | −1 | 1 |
| 19 | 0 | None | −1 | −1 | −1 |
| 20 | 1 | None | 0 | 0 | 1 |

What is claimed is:

1. A method of decreasing aggregation of a recombinant glycoprotein expressed in Chinese Hamster Ovary (CHO) cells under suitable cell culture conditions comprising:
adding 1 mg/L-100 mg/L of Zinc, 1.05 g/L-2 g/L Asparagine and 0.1 g-1.05 g/L Aspartic to the cell culture medium,
wherein the cell culture medium is maintained under following conditions:
a) pH between 6.5-7.5;
b) dissolved oxygen between 5% and 90% of air saturation;
c) carbon dioxide between 10 mmHg and 150 mmHg; and
d) temperature between 30° C. and 37° C.; and
and wherein the level of aggregation of the expressed glycoprotein is decreased.

2. The method of claim 1, wherein the cell culture medium is chemically defined.

3. The method of claim 2, wherein the chemically defined cell culture medium is basal medium.

4. The method of claim 3, wherein the chemically defined basal medium does not contain added serum or hydrolysates.

5. The method of claim 3, wherein the chemically defined basal medium is protein-free.

6. The method according to claim 1, wherein the glycoprotein is a recombinant antibody, antibody fragment or fusion protein.

7. The method according to claim 1, wherein the cell culture process is performed under batch, fed-batch or continuous cell culture conditions.

* * * * *